(12) United States Patent
Dunn-Coleman et al.

(10) Patent No.: US 7,037,704 B2
(45) Date of Patent: May 2, 2006

(54) **HETEROLOGOUS EXPRESSION OF AN *ASPERGILLUS KAWACHI* ACID-STABLE ALPHA AMYLASE AND APPLICATIONS IN GRANULAR STARCH HYDROLYSIS**

(75) Inventors: Nigel Dunn-Coleman, Los Gatos, CA (US); Oreste J. Lantero, Jr., Belvidere, IL (US); Suzanne E. Lantz, San Carlos, CA (US); Michael J. Pepsin, Castro Valley, CA (US); Jayarama K. Shetty, Pleasanton, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 10/999,886

(22) Filed: Nov. 30, 2004

(65) Prior Publication Data

US 2005/0266543 A1    Dec. 1, 2005

Related U.S. Application Data

(60) Provisional application No. 60/605,437, filed on Aug. 30, 2004, provisional application No. 60/575,175, filed on May 27, 2004.

(51) Int. Cl.
| | |
|---|---|
| *C12N 15/56* | (2006.01) |
| *C12N 9/28* | (2006.01) |
| *C12N 9/30* | (2006.01) |
| *C12N 9/34* | (2006.01) |

(52) U.S. Cl. .................. 435/202; 435/203; 435/205

(58) Field of Classification Search ............. 435/202, 435/203, 205, 913
See application file for complete search history.

(56) References Cited

OTHER PUBLICATIONS

Kajiwara, Y. et al., Production of Acid-Stable α-Amylase by *Aspergillus kawachii* during Barley *Shochu-Koji* Production, *Journal of Fermentation and Bioengineering*, 84(3): 224-227, 1997.
Copy of the International Search Report for PCT/US04/41276, filed Dec. 9, 2004.

*Primary Examiner*—Tekchand Saidha
(74) *Attorney, Agent, or Firm*—Genencor International, Inc.

(57) ABSTRACT

The present invention relates to a granular starch hydrolyzing enzyme composition comprising an acid stable alpha amylase (asAA) having granular starch hydrolyzing activity. The invention also relates to a one-step method for producing an alcohol which comprises contacting a granular starch substrate with an acid-stable alpha amylase (asAA) having granular starch hydrolyzing (GSH) activity and a glucoamylase (GA) in a fermentation step which also comprises ethanologenic microorganisms at a temperature of 25–40° C. to obtain a fermentation broth having 5 to 20% ethanol.

14 Claims, 13 Drawing Sheets

ATGAGAGTGTCGACTTCAAGTATTGCCCTTGCTGTGTCCCTTTTTGGGAAGCTGGCCCTTGGG
CTGTCAGCTGCAGAATGGCGCACTCAATCCATCTACTTCCTTTTGACGGATCGGTTCGGTAGG
ACGGACAATTCGACTACAGCTACGTGCAATACGGGTGACCA<u>AGTATGGTATTGCTGTACTTCC
GTCATTCATCTGCTGACTTGGATAG</u>ATCTACTGTGGTGGAAGTTGGCAAGGAATTATCAACCA
T<u>GTTCGTATCTCACTTCATACCATCCATGCTGGGCGCTTCTGACTATTGCTCCAG</u>CTGGACTA
TATCCAGGGCATGGGATTCACAGCTATCTGGATCTCGCCTATCACTGAGCAGCTACCCCAGGA
TACTTCGGATGGTGAAGCCTACCATGGATACTGGCAGCAGAAGA<u>TGTATGCCCTCATTGCATT
CATATTTTATGCTTACTCGCAGACTGCAGCTGACTTGGCAG</u>ATACAATGTGAACTCCAACTTC
GGCACGGCAGATGATCTGAAGTCCCTCTCCGATGCTCTTCACGCCCGCGGAATGTACCTCATG
GTCGACGTCGTCCCTAACCACATG<u>GTAAGTACTGCTTTACCTCTATATTAGTAAACCCAATGC
GAACAATGACTGTATCAG</u>GGCTACGCAGGTAACGGCAACGATGTGGATTACAGCGTCTTCGAC
CCCTTCGACTCCTCCTCCTACTTCCATCCATACTGCCTCATCACAGATTGGGACAACTTGACC
ATGGTCCAAGACTGTTGGGAGGGTGACACCATCGTGTCTCTGCCAGATCTGAACACCACGGAA
ACCGCCGTGAGAACCATTTGGTACGATTGGGTAGCCGACCTGGTATCCAACTACTCAG<u>GTGCG
ACCCCAACCCACTAAAACAAGCCACATACTAAAAAATTGCTCAG</u>TCGACGGCCTCCGTATCGA
CAGTGTCGAAGAAGTCGAACCCGACTTCTTCCCGGGCTACCAAGAAGCAGCAGGAGTCTACTG
CGTCGGTGAAGTCGACAACGGCAACCCTGCTCTCGACTGCCCATACCAAAAATATCTAGATGG
TGTTCTCAACTATCCAT<u>GTACATACCCCTTCTACCTTCTCGAACCCATCACTAACTCAATT
GCTGCAG</u>CTACTGGCAACTCCTCTACGCCTTTGAATCCTCCAGCGGCAGCATCAGCAACCTCT
ACAACATGATCAAATCCGTCGCCAGCGACTGCTCCGATCCGACCCTCCTGGGCAACTTTATCG
AAAACCACGACAACCCCGCTTCGCCTC<u>GTATGTCCCTTCCATCACTGCCCCCTTTTAAAGTA
AACCCCACTGACAGGCAAAG</u>CTACACATCCGACTACTCCCAAGCCAAAAACGTCCTCAGCTAC
ATCTTCCTCTCCGACGGCATCCCCATCGTCTACGCCGGCGAAGAACAGCACTACTCCGGCGGC
GACGTGCCCTACAACCGCGAAGCTACCTGGCTATCAGGCTACGACACCTCCGCGGAGCTCTAC
ACCTGGATAGCCACCACAAACGCGATCCGGAAACTAGCTATCTCAGCAGACTCGGACTACATT
ACTTACGCGG<u>TTTGCCCTTTCCCTTCCCCCCACCCAGAGCTCAACCCCCATTCTAACAAAATA
TTTCAATGGTAG</u>AA

FIG. 1A

CGACCCAATCTACACAGACAGCAACACCATCGCGATGCGCAAAGGCACCTCCGGCTCCCAAAT
CATCACCGTCCTCTCCAACAAAGGCTCCTCCGGAAGCAGCTACACCCTCACCCTCAGCGGAAG
CGGCTACACGTCCGGCACGAAGCTCATCGAAGCGTACACCTGCACGTCCGTGACGGTGGACTC
GAACGGGGATATCCCTGTGCCGATGGCTTCGGGATTACCTAGAGTTCTCCTCCCTGCTTCGGT
GGTTGATAGTTCTTCGCTTTGTGGGGGAGTGGTAACACAACCACGACCACAACTGCTGCTAC
CTCCACATCCAAAGCCACCACCTCCTCTTCTTCTTCTGCTGCTGCTACTACTTCTTCATC
ATGCACCGCAACAAGCACCACCCTCCCCATCACCTTCGAAGAACTCGTCACCACTACCTACGG
GGAAGAAGTCTACCTCAGCGGATCTATCTCCCAGCTCGGAGAGTGGGATACGAGTGACGCGGT
GAAGTTGTCCGCGGATGATTATACCTCGAGTAACCCCGAGTGGTCTGTTACTGTGTCGTTGCC
GGTGGGGACGACCTTCGAGTATAAGTTTATTAAGGTCGATGAGGGTGGAAGTGTGACTTGGGA
AAGTGATCCGAATAGGGAGTATACTGTGCCTGAATGTGGGAGTGGGAGTGGGGAGACGGTGGT
TGATACGTGGAGGTAG

FIG. 1B

SEQ ID NO. 4

MRVSTSSIALAVSLFGKLALGLSAAEWRTQSIYFLLTDRFGRTDNSTTATCNTGDQIYCGGSW
QGIINHLDYIQGMGFTAIWISPITEQLPQDTSDGEAYHGYWQQKIYNVNSNFGTADDLKSLSD
ALHARGMYLMVDVVPNHMGYAGNGNDVDYSVFDPFDSSSYFHPYCLITDWDNLTMVQDCWEGD
TIVSLPDLNTTETAVRTIWYDWVADLVSNYSVDGLRIDSVEEVEPDFFPGYQEAAGVYCVGEV
DNGNPALDCPYQKYLDGVLNYPIYWQLLYAFESSSGSISNLYNMIKSVASDCSDPTLLGNFIE
NHDNPRFASYTSDYSQAKNVLSYIFLSDGIPIVYAGEEQHYSGGDVPYNREATWLSGYDTSAE
LYTWIATTNAIRKLAISADSDYITYANDPIYTDSNTIAMRKGTSGSQIITVLSNKGSSGSSYT
LTLSGSGYTSGTKLIEAYTCTSVTVDSNGDIPVPMASGLPRVLLPASVVDSSSLCGGSGNTTT
TTTAATSTSKATTSSSSSSAAATTSSSCTATSTTLPITFEELVTTTYGEEVYLSGSISQLGEW
DTSDAVKLSADDYTSSNPEWSVTVSLPVGTTFEYKFIKVDEGGSVTWESDPNREYTVPECGSG
SGETVVDTWR

*FIG. 2*

SEQ ID NO. 5

CTGCAGCCACTTGCAGTCCCGTGGAATTCTCACGGTGAATGTAGGCCTTTTGTAGGGTAGGAA
TTGTCACTCAAGCACCCCCAACCTCCATTACGCCTCCCCCATAGAGTTCCCAATCAGTGAGTC
ATGGCACTGTTCTCAAATAGATTGGGGAGAAGTTGACTTCCGCCCAGAGCTGAAGGTCGCACA
ACCGCATGATATAGGGTCGGCAACGGCAAAAAGCACGTGGCTCACCGAAAAGCAAGATGTTT
GCGATCTAACATCCAGGAACCTGGATACATCCATCATCACGCACGACCACTTTGATCTGCTGG
TAAACTCGTATTCGCCCTAAACCGAAGTGCGTGGTAAATCTACACGTGGGCCCCTTTCGGTAT
ACTGCGTGTGTCTTCTCTAGGTGCCATTCTTTTCCCTTCCTCTAGTGTTGAATTGTTTGTGTT
GGAGTCCGAGCTGTAACTACCTCTGAATCTCTGGAGAATGGTGGACTAACGACTACCGTGCAC
CTGCATCATGTATATAATAGTGATCCTGAGAAGGGGGGTTTGGAGCAATGTGGGACTTTGATG
GTCATCAAACAAAGAACGAAGACGCCTCTTTTGCAAAGTTTTGTTTCGGCTACGGTGAAGAAC
TGGATACTTGTTGTGTCTTCTGTGTATTTTTGTGGCAACAAGAGGCCAGAGACAATCTATTCA
ACACCAAGCTTGCTCTTTTGAGCTACAAGAACCTGTGGGGTATATATCTAGAGTTGTGAAGT
CGGTAATCCCGCTGTATAGTAATACGAGTCGCATCTAAATACTCCGAAGCTGCTGCGAACCCG
GAGAATCGAGATGTGCTGGAAAGCTTCTAGCGAGCGGCTAAATTAGCATGAAAGGCTATGAGA
AATTCTGGAGACGGCTTGTTGAATCATGGCGTTCCATTCTTCGACAAGCAAAGCGTTCCGTCG
CAGTAGCAGGCACTCATTCCCGAAAAAACTCGGAGATTCCTAAGTAGCGATGGAACCGGAATA
ATATAATAGGCAATACATTGAGTTGCCTCGACGGTTGCAATGCAGGGGTACTGAGCTTGGACA
TAACTGTTCCGTACCCCACCTCTTCTCAACCTTTGGCGTTTCCCTGATTCAGCGTACCCGTAC
AAGTCGTAATCACTATTAACCCAGACTGACCGGACGTGTTTTGCCCTTCATTTGGAGAAATAA
TGTCATTGCGATGTGTAATTTGCCTGCTTGACCGACTGGGGCTGTTCGAAGCCCGAATGTAGG
ATTGTTATCCGAACTCTGCTCGTAGAGGCATGTTGTGAATCTGTGTCGGGCAGGACACGCCTC
GAAGGTTCACGGCAAGGGAAACCACCGATAGCAGTGTCTAGTAGCAACCTGTAAAGCCGCAAT
GCAGCATCACTGGAAAATACAAACCAATGGCTAAAAGTACATAAGTTAATGCCTAAAGAAGTC
ATATACCAGCGGCTAATAATTGTACAATCAAGTGGCTAAACGTACCGTAATTTGCCAACGGCT
TGTGGGGTTGCAGAAGCAACGGCAAAGCCCCACTTCCCCACGTTTGTTTCTTCACTCAGTCCA
ATCTCAGCTGGTGATCCCCCAATTGGGTCGCTTGTTTGTTCCGGTGAAGTGAAAGAAGACAGA
GGTAAGAATGTCTGACTCGGAGCGTTTTGCATACAACCAAGGGCAGTGATGGAAGACAGTGAA
ATGTTGACATTCAAGGAGTATTTAGCCAGGGATGCTTGAGTGTATCGTGTAAGGAGGTTTGTC
TGCCGATACGACGAATACTGTATAGTCACTTCTGATGAAGTGGTCCATATTGAAATGTAAGTC
GGCACTGAACAGGCAAAAGATTGAGTTGAAACTGCCTAAGATCTCGGGCCCTCGGGCCTTCGG

*FIG. 3A*

```
CCTTTGGGTGTACATGTTTGTGCTCCGGGCAAATGCAAAGTGTGGTAGGATCGAACACACTGC
TGCCTTTACCAAGCAGCTGAGGGTATGTGATAGGCAAATGTTCAGGGGCCACTGCATGGTTTC
GAATAGAAAGAGAAGCTTAGCCAAGAACAATAGCCGATAAAGATAGCCTCATTAAACGGAATG
AGCTAGTAGGCAAAGTCAGCGAATGTGTATATATAAAGGTTCGAGGTCCGTGCCTCCCTCATG
CTCTCCCCATCTACTCATCAACTCAGATCCTCCAGGAGACTTGTACACCATCTTTTGAGGCAC
AGAAACCCAATAGTCAACCATCACAAGTTTGTACAAAAAAGCAGGCTCCGCGGCCGCCCCCTT
CAcCATGAGAGTGTCGACTTCAAGTATTGCCCTTGCTGTGTCCCTTTTTGGGAAGCTGGCCCT
TGGGCTGTCAGCTGCAGAATGGCGCACTCAATCCATCTACTTCCTTTTGACGGATCGGTTCGG
TAGGACGGACAATTCGACTACAGCTACGTGCAATACGGGTGACCAAGTATGGTATTGCTGTAC
TTCCGTCATTCATCTGCTGACTTGGATAGATCTACTGTGGTGGAAGTTGGCAAGGAATTATCA
ACCATGTTCGTATCTCACTTCATACCATCCATGCTGGGCGCTTCTGACTATTGCTCCAGCTGG
ACTATATCCAGGGCATGGGATTCACAGCTATCTGGATCTCGCCTATCACTGAGCAGCTACCCC
AGGATACTTCGGATGGTGAAGCCTACCATGGATACTGGCAGCAGAAGATGTATGCCCTCATTG
CATTCATATTTTATGCTTACTCGCAGACTGCAGCTGACTTGGAGATACAATGTGAACTCCAA
CTTCGGCACGGCAGATGATCTGAAGTCCCTCTCCGATGCTCTTCACGCCCGCGGAATGTACCT
CATGGTCGACGTCGTCCCTAACCACATGGTAAGTACTGCTTTACCTCTATATTAGTAAACCCA
ATGCGAACAATGACTGTATCAGGGCTACGCAGGTAACGGCAACGATGTGGATTACAGCGTCTT
CGACCCCTTCGACTCCTCCTCCTACTTCCATCCATACTGCCTCATCACAGATTGGGACAACTT
GACCATGGTCCAAGACTGTTGGGAGGGTGACACCATCGTGTCTCTGCCAGATCTGAACACCAC
GGAAACCGCCGTGAGAACCATTTGGTACGATTGGGTAGCCGACCTGGTATCCAACTACTCAGG
TGCGACCCCAACCCACTAAAACAAGCCACATACTAAAAAATTGCTCAGTCGACGGCCTCCGTA
TCGACAGTGTCGAAGAAGTCGAACCCGACTTCTTCCCGGGCTACCAAGAAGCAGCAGGAGTCT
ACTGCGTCGGTGAAGTCGACAACGGCAACCCTGCTCTCGACTGCCCATACCAAAAATATCTAG
ATGGTGTTCTCAACTATCCCATGTACATACCCCCTTCTACCTTCTCGAACCCATCACTAACTC
AATTGCTGCAGCTACTGGCAACTCCTCTACGCCTTTGAATCCTCCAGCGGCAGCATCAGCAAC
CTCTACAACATGATCAAATCCGTCGCCAGCGACTGCTCCGATCCGACCCTCCTGGGCAACTTT
ATCGAAAACCACGACAACCCCCGCTTCGCCTCGTATGTCCCTTCCATCACTGCCCCCTTTTAA
AGTAAACCCCACTGACAGGCAAAGCTACACATCCGACTACTCCCAAGCCAAAAACGTCCTCAG
CTACATCTTCCTCTCCGACGGCATCCCCATCGTCTACGCCGGCGAAGAACAGCACTACTCCGG
CGGCGACGTGCCCTACAACCGCGAAGCTACCTGGCTATCAGGCTACGACACCTCCGCGGAGCT
CTACACCTGGATAGCCACCACAAACGCGATCCGGAAACTAGCTATCTCAGCAGACTCGGACTA
CATTACTTACGCGGTTTGCCCTTTCCCTTCCCCCCACCCAGAGCTCAACCCCCATTCTAACAA
AATATTTCAATGGTAGAACGACCCAATCTACACAGACAGCAACACCATCGCGATGCGCAAAGG
CACCTCCGGCTCCCAAATCATCACCGTCCTCTCCAACAAAGGCTCCTCCGGAAGCAGCTACAC
CCTCACCCTCAGCGGAAGCGGCTACACGTCCGGCACGAAGCTCATCGAAGCGTACACCTGCAC
GTCCGTGACGGTGGACTCGAACGGGGATATCCCTGTGCCGATGGCTTCGGGATTACCTAGAGT
TCTCCTCCCTGCTTCGGTGGTTGATAGTTCTTCGCTTTGTGGGGGAGTGGTAACACAACCAC
GACCACAACTGCTGCTACCTCCACATCCAAAGCCACCACCTCCTCTTCTTCTTCTTCTGCTGC
TGCTACTACTTCTTCATCATGCACCGCAACAAGCACCACCCTCCCCATCACCTTCGAAGAACT
CGTCACCACTACCTACGGGGAAGAAGTCTACCTCAGCGGATCTATCTCCCAGCTCGGAGAGTG
GGATACGAGTGACGCGGTGAAGTTGTCCGCGGATGATTATACCTCGAGTAACCCCGAGTGGTC
TGTTACTGTGTCGTTGCCGGTGGGGACGACCTTCGAGTATAAGTTTATTAAGGTCGATGAGGG
TGGAAGTGTGACTTGGGAAAGTGATCCGAATAGGGAGTATACTGTGCCTGAATGTGGGAGTGG
GAGTGGGGAGACGGTGGTTGATACGTGGAGGTAGAAGGGTGGGCGCGCCGACCCAGCTTTctt
gtacaaagtggtgatcgcgccAGCTCCGTGCGAAAGCCTGACGCACCGGTAGATTCTTGGTGA
GCCCGTATCATGACGGCGGCGGGAGCTACATGGCCCCGGGTGATTTATTTTTTTGTATCTAC
TTCTGACCCTTTTCAAATATACGGTCAACTCATCTTTCACTGGAGATGCGGCCTGCTTGGTAT
TGCGATGTTGTCAGCTTGGCAAATTGTGGCTTTCGAAAACACAAAACGATTCCTTAGTAGCCA
TGCATTTTAAGATAACGGAATAGAAGAAAGAGGAAATTAAAAAAAAAAAAAAAACAAACATCC
```

*FIG. 3B*

```
CGTTCATAACCCGTAGAATCGCCGCTCTTCGTGTATCCCAGTACCAGTTTATTTTGAATAGCT
CGCCCGCTGGAGAGCATCCTGAATGCAAGTAACAACCGTAGAGGCTGACACGGCAGGTGTTGC
TAGGGAGCGTCGTGTTCTACAAGGCCAGACGTCTTCGCGGTTGATATATATGTATGTTTGACT
GCAGGCTGCTCAGCGACGACAGTCAAGTTCGCCCTCGCTGCTTGTGCAATAATCGCAGTGGGG
AAGCCACACCGTGACTCCCATCTTTCAGTAAAGCTCTGTTGGTGTTTATCAGCAATACACGTA
ATTTAAACTCGTTAGCATGGGGCTGATAGCTTAATTACCGTTTACCAGTGCCATGGTTCTGCA
GCTTTCCTTGGCCCGTAAAATTCGGCGAAGCCAGCCAATCACCAGCTAGGCACCAGCTAAACC
CTATAATTAGTCTCTTATCAACACCATCCGCTCCCCGGGATCAATGAGGAGAATGAGGGGGA
TGCGGGCTAAAGAAGCCTACATAACCCTCATGCCAACTCCCAGTTTACACTCGTCGAGCCAA
CATCCTGACTATAAGCTAACACAGAATGCCTCAATCCTGGGAAGAACTGGCCGCTGATAAGCG
CGCCCGCCTCGCAAAAACCATCCCTGATGAATGGAAAGTCCAGACGCTGCCTGCGGAAGACAG
CGTTATTGATTTCCCAAAGAAATCGGGGATCCTTTCAGAGGCCGAACTGAAGATCACAGAGGC
CTCCGCTGCAGATCTTGTGTCCAAGCTGGCGGCCGGAGAGTTGACCTCGGTGGAAGTTACGCT
AGCATTCTGTAAACGGGCAGCAATCGCCCAGCAGTTAGTAGGGTCCCCTCTACCTCTCAGGGA
GATGTAACAACGCCACCTTATGGGACTATCAAGCTGACGCTGGCTTCTGTGCAGACAAACTGC
GCCCACGAGTTCTTCCCTGACGCCGCTCTCGCGCAGGCAAGGGAACTCGATGAATACTACGCA
AAGCACAAGAGACCCGTTGGTCCACTCCATGGCCTCCCCATCTCTCTCAAAGACCAGCTTCGA
GTCAAGGTACACCGTTGCCCCTAAGTCGTTAGATGTCCCTTTTTGTCAGCTAACATATGCCAC
CAGGGCTACGAAACATCAATGGGCTACATCTCATGGCTAAACAAGTACGACGAAGGGGACTCG
GTTCTGACAACCATGCTCCGCAAAGCCGGTGCCGTCTTCTACGTCAAGACCTCTGTCCCGCAG
ACCCTGATGGTCTGCGAGACAGTCAACAACATCATCGGGCGCACCGTCAACCCACGCAACAAG
AACTGGTCGTGCGGCGGCAGTTCTGGTGGTGAGGGTGCGATCGTTGGGATTCGTGGTGGCGTC
ATCGGTGTAGGAACGGATATCGGTGGCTCGATTCGAGTGCCGGCCGCGTTCAACTTCCTGTAC
GGTCTAAGGCCGAGTCATGGGCGGCTGCCGTATGCAAAGATGGCGAACAGCATGGAGGGTCAG
GAGACGGTGCACAGCGTTGTCGGGCCGATTACGCACTCTGTTGAGGGTGAGTCCTTCGCCTCT
TCCTTCTTTTCCTGCTCTATACCAGGCCTCCACTGTCCTCCTTTCTTGCTTTTTATACTATAT
ACGAGACCGGCAGTCACTGATGAAGTATGTTAGACCTCCGCCTCTTCACCAAATCCGTCCTCG
GTCAGGAGCCATGGAAATACGACTCCAAGGTCATCCCCATGCCCTGGCGCCAGTCCGAGTCGG
ACATTATTGCCTCCAAGATCAAGAACGGCGGGCTCAATATCGGCTACTACAACTTCGACGGCA
ATGTCCTTCCACACCCTCCTATCCTGCGCGGCGTGGAAACCACCGTCGCCGCACTCGCCAAAG
CCGGTCACACCGTGACCCCGTGGACGCCATACAAGCACGATTTCGGCCACGATCTCATCTCCC
ATATCTACGCGGCTGACGGCAGCGCCGACGTAATGCGCGATATCAGTGCATCCGGCGAGCCGG
CGATTCCAAATATCAAAGACCTACTGAACCCGAACATCAAAGCTGTTAACATGAACGAGCTCT
GGGACACGCATCTCCAGAAGTGGAATTACCAGATGGAGTACCTTGAGAAATGGCGGGAGGCTG
AAGAAAAGGCCGGGAAGGAACTGGACGCCATCATCGCGCCGATTACGCCTACCGCTGCGGTAC
GGCATGACCAGTTCCGGTACTATGGGTATGCCTCTGTGATCAACCTGCTGGATTTCACGAGCG
TGGTTGTTCCGGTTACCTTTGCGGATAAGAACATCGATAAGAAGAATGAGAGTTTCAAGGCGG
TTAGTGAGCTTGATGCCCTCGTGCAGGAAGAGTATGATCCGGAGGCGTACCATGGGGCACCGG
TTGCAGTGCAGGTTATCGGACGGAGACTCAGTGAAGAGAGGACGTTGGCGATTGCAGAGGAAG
TGGGGAAGTTGCTGGGAAATGTGGTGACTCCATAGCTAATAAGTGTCAGATAGCAATTTGCAC
AAGAAATCAATACCAGCAACTGTAAATAAGCGCTGAAGTGACCATGCCATGCTACGAAAGAGC
AGAAAAAAACCTGCCGTAGAACCGAAGAGATATGACACGCTTCCATCTCTCAAAGGAAGAATC
CCTTCAGGGTTGCGTTTCCAGTCTAGACACGTATAACGGCACAAGTGTCTCTCACCAAATGGG
TTATATCTCAAATGTGATCTAAGGATGGAAAGCCCAGAATATCGATCGCGCGCAGATCCATAT
ATAGGGCCCGGGTTATAATTACCTCAGGTCGACGTCCCATGGCCATTCGAATTCGTAATCATG
GTCATAGCTGTTTCCTGTGTGAAATTGTTATCCGCTCACAATTCCACACAACATACGAGCCGG
AAGCATAAAGTGTAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATGAATCGGCCAACG
CGCGGGGAGAGGCGGTTTGCGTATTGGGCGCTCTTCCGCTTCCTCGCTCACTGACTCGCTGCG
```

FIG. 3C

```
CTCGGTCGTTCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCGTTCAGCCCGACCGCTGCGCCTT
ATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGAAGCCAGTTAC
CTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATT
ATCAAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAGC
GATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCC
AGATTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTAT
GGCTTCATTCAGCTCCGGTTCCCAACGATCAAGGCGAGTTACATGATCCCCCATGTTGTGCAA
AAAAGCGGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTGCTC
TTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGAT
GTAACCCACTCGTGCACCCAACTGATCTTCAGCATCTTTTACTTTCACCAGCGTTTCTGGGTG
AGCAAAAACAGGAAGGCAAAATGCCGCAAAAAAGGGAATAAGGGCGACACGGAAATGTTGAAT
ACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAA
AGTGCCACCTGACGTCTAAGAAACCATTATTATCATGACATTAACCTATAAAAATAGGCGTAT
CACGAGGCCCTTTCGTCTCGCGCGTTTCGGTGATGACGGTGAAAACCTCTGACACATGCAGCT
CCCGGAGACGGTCACAGCTTGTCTGTAAGCGGATGCCGGGAGCAGACAAGCCCGTCAGGGCGC
GTCAGCGGGTGTTGGCGGGTGTCGGGCTGGCTTAACTATGCGGCATCAGAGCAGATTGTACT
GAGAGTGCACCATAAAATTGTAAACGTTAATATTTTGTTAAAATTCGCGTTAAATTTTTGTTA
AATCAGCTCATTTTTTAACCAATAGGCCGAAATCGGCAAAATCCCTTATAAATCAAAAGAATA
GCCCGAGATAGGGTTGAGTGTTGTTCCAGTTTGGAACAAGAGTCCACTATTAAAGAACGTGGA
CTCCAACGTCAAAGGGCGAAAAACCGTCTATCAGGGCGATGGCCCACTACGTGAACCATCACC
CAAATCAAGTTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGAAGAAAGCGAA
AGGAGCGGGCGCTAGGGCGCTGGCAAGTGTAGCGGTCACGCTGCGCGTAACCACCACACCCGC
CGCGCTTAATGCGCCGCTACAGGGCGCGTACTATGGTTGCTTTGACGTATGCGGTGTGAAATA
CCGCACAGATGCGTAAGGAGAAAATACCGCATCAGGCGCCATTCGCCATTCAGGCTGCGCAAC
TGTTGGGAAGGGCGATCGGTGCGGGCCTCTTCGCTATTACGCCAGCTGGCGAAAGGGGGATGT
GCTGCAAGGCGATTAAGTTGGGTAACGCCAGGGTTTTCCCAGTCACGACGTTGTAAAACGACG
GCCAGTGCCCAAGCTTACTAGTACTTCTCGAGCTCTGTACATGTCCGGTCGCGACGTACGCGT
ATCGATGGCGCCAGCTGCAGGCGGCCGC
```

FIG. 3D

SEQUENCE LISTING

<160> NUMBER OF SEQ ID NOS: 7

<210> SEQ ID NO 1
<211> LENGTH: 2361
<212> TYPE: DNA
<213> ORGANISM: Aspergillus kawachi

<400> SEQUENCE: 1

| | | | | | |
|---|---|---|---|---|---|
| atgagagtgt | cgacttcaag | tattgccctt | gctgtgtccc | tttttgggaa | gctggcccttt | 60 |
| gggctgtcag | ctgcagaatg | gcgcactcaa | tccatctact | tccttttgac | ggatcggttc | 120 |
| ggtaggacgg | acaattcgac | tacagctacg | tgcaatacgg | gtgaccaagt | atggtattgc | 180 |
| tgtacttccg | tcattcatct | gctgacttgg | atagatctac | tgtggtggaa | gttggcaagg | 240 |
| aattatcaac | catgttcgta | tctcacttca | taccatccat | gctgggcgct | tctgactatt | 300 |
| gctccagctg | gactatatcc | agggcatggg | attcacagct | atctggatct | cgcctatcac | 360 |
| tgagcagcta | ccccaggata | cttcggatgg | tgaagcctac | catggatact | ggcagcagaa | 420 |
| gatgtatgcc | ctcattgcat | tcatatttta | tgcttactcg | cagactgcag | ctgacttggc | 480 |
| agatacaatg | tgaactccaa | cttcggcacg | gcagatgatc | tgaagtccct | ctccgatgct | 540 |
| cttcacgccc | gcggaatgta | cctcatggtc | gacgtcgtcc | ctaaccacat | ggtaagtact | 600 |
| gctttacctc | tatattagta | aacccaatgc | gaacaatgac | tgtatcaggg | ctacgcaggt | 660 |
| aacggcaacg | atgtggatta | cagcgtcttc | gaccccttcg | actcctcctc | ctacttccat | 720 |
| ccatactgcc | tcatcacaga | ttgggacaac | ttgaccatgg | tccaagactg | ttgggagggt | 780 |
| gacaccatcg | tgtctctgcc | agatctgaac | accacggaaa | ccgccgtgag | aaccatttgg | 840 |
| tacgattggg | tagccgacct | ggtatccaac | tactcaggtg | cgaccccaac | ccactaaaac | 900 |
| aagccacata | ctaaaaaatt | gctcagtcga | cggcctccgt | atcgacagtg | tcgaagaagt | 960 |
| cgaacccgac | ttcttcccgg | gctaccaaga | agcagcagga | gtctactgcg | tcggtgaagt | 1020 |
| cgacaacggc | aaccctgctc | tcgactgccc | ataccaaaaa | tatctagatg | gtgttctcaa | 1080 |
| ctatcccatg | tacataccc | cttctacctt | ctcgaaccca | tcactaactc | aattgctgca | 1140 |
| gctactggca | actcctctac | gcctttgaat | cctccagcgg | cagcatcagc | aacctctaca | 1200 |
| acatgatcaa | atccgtcgcc | agcgactgct | ccgatccgac | cctcctgggc | aactttatcg | 1260 |
| aaaaccacga | caaccccgc | ttcgcctcgt | atgtccttc | catcactgcc | cccttttaaa | 1320 |
| gtaaacccca | ctgacaggca | aagctacaca | tccgactact | cccaagccaa | aaacgtcctc | 1380 |
| agctacatct | tcctctccga | cggcatcccc | atcgtctacg | ccggcgaaga | acagcactac | 1440 |
| tccggcggcg | acgtgcccta | caaccgcgaa | gctacctggc | tatcaggcta | cgacacctcc | 1500 |
| gcggagctct | acacctggat | agccaccaca | aacgcgatcc | ggaaactagc | tatctcagca | 1560 |
| gactcggact | acattactta | caaggtttgc | cctttccctt | ccccccaccc | agagctcaac | 1620 |
| ccccattcta | acaaaatatt | tcaatggtag | aacgacccaa | tctacacaga | cagcaacacc | 1680 |
| atcgcgatgc | gcaaaggcac | ctccggctcc | caaatcatca | ccgtcctctc | caacaaaggc | 1740 |
| tcctccggaa | gcagctacac | cctcacccte | agcggaagcg | gctacacgtc | cggcacgaag | 1800 |
| ctcatcgaag | cgtacacctg | cacgtccgtg | acggtggact | cgaacgggga | tatccctgtg | 1860 |
| ccgatggctt | cgggattacc | tagagttctc | ctccctgctt | cggtggttga | tagttcttcg | 1920 |
| ctttgtgggg | ggagtggtaa | cacaaccacg | accacaactg | ctgctacctc | cacatccaaa | 1980 |
| gccaccacct | cctcttcttc | ttcttctgct | gctgctacta | cttcttcatc | atgcaccgca | 2040 |

```
acaagcacca ccctccccat caccttcgaa gaactcgtca ccactaccta cggggaagaa    2100
gtctacctca gcggatctat ctcccagctc ggagagtggc atacgagtga cgcggtgaag    2160
ttgtccgcgg atgattatac ctcgagtaac cccgagtggt ctgttactgt gtcgttgccg    2220
gtggggacga ccttcgagta taagtttatt aaggtcgatg agggtggaag tgtgacttgg    2280
gaaagtgatc cgaataggga gtatactgtg cctgaatgtg ggagtgggag tggggagacg    2340
gtggttgata cgtggaggta g                                              2361
```

<210> SEQ ID NO 2
<211> LENGTH: 21
<212> TYPE: PRT
<213> ORGANISM: Aspergillus kawachi

<400> SEQUENCE: 2

```
Met Arg Val Ser Thr Ser Ser Ile Ala Leu Ala Val Ser Leu Phe Gly
1               5                   10                  15

Lys Leu Ala Leu Gly
            20
```

<210> SEQ ID NO 3
<211> LENGTH: 619
<212> TYPE: PRT
<213> ORGANISM: Aspergillus kawachi

<400> SEQUENCE: 3

```
Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Ala Thr Cys Asn Thr
            20                  25                  30

Gly Asp Gln Ile Tyr Cys Gly Gly Ser Trp Gln Gly Ile Ile Asn His
            35                  40                  45

Leu Asp Tyr Ile Gln Gly Met Gly Phe Thr Ala Ile Trp Ile Ser Pro
50                  55                  60

Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
            85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
            115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
            165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
            195                 200                 205

Glu Glu Val Glu Pro Asp Phe Phe Pro Gly Tyr Gln Glu Ala Ala Gly
            210                 215                 220

Val Tyr Cys Val Gly Glu Val Asp Asn Gly Asn Pro Ala Leu Asp Cys
225                 230                 235                 240
```

-continued

```
Pro Tyr Gln Lys Tyr Leu Asp Gly Val Leu Asn Tyr Pro Ile Tyr Trp
                245                 250                 255

Gln Leu Leu Tyr Ala Phe Glu Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Gln His Tyr Ser
                325                 330                 335

Gly Gly Asp Val Pro Tyr Asn Arg Glu Ala Thr Trp Leu Ser Gly Tyr
                340                 345                 350

Asp Thr Ser Ala Glu Leu Tyr Thr Trp Ile Ala Thr Asn Ala Ile
            355                 360                 365

Arg Lys Leu Ala Ile Ser Ala Asp Ser Asp Tyr Ile Thr Tyr Ala Asn
    370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
                405                 410                 415

Ser Ser Tyr Thr Leu Thr Leu Ser Gly Ser Gly Thr Tyr Ser Gly Thr
            420                 425                 430

Lys Leu Ile Glu Ala Tyr Thr Cys Thr Ser Val Thr Val Asp Ser Asn
        435                 440                 445

Gly Asp Ile Pro Val Pro Met Ala Ser Gly Leu Pro Arg Val Leu Leu
    450                 455                 460

Pro Ala Ser Val Val Asp Ser Ser Leu Cys Gly Gly Ser Gly Asn
465                 470                 475                 480

Thr Thr Thr Thr Thr Thr Ala Ala Thr Ser Thr Ser Lys Ala Thr Thr
                485                 490                 495

Ser Ser Ser Ser Ser Ser Ala Ala Thr Thr Ser Ser Cys Thr
            500                 505                 510

Ala Thr Ser Thr Thr Leu Pro Ile Thr Phe Glu Glu Leu Val Thr Thr
        515                 520                 525

Thr Tyr Gly Glu Glu Val Tyr Leu Ser Gly Ser Ile Ser Gln Leu Gly
    530                 535                 540

Glu Trp Asp Thr Ser Asp Ala Val Lys Leu Ser Ala Asp Tyr Thr
545                 550                 555                 560

Ser Ser Asn Pro Glu Trp Ser Val Thr Val Ser Leu Pro Val Gly Thr
                565                 570                 575

Thr Phe Glu Tyr Lys Phe Ile Lys Val Asp Glu Gly Gly Ser Val Thr
            580                 585                 590

Trp Glu Ser Asp Pro Asn Arg Glu Tyr Thr Val Pro Glu Cys Gly Ser
        595                 600                 605

Gly Ser Gly Glu Thr Val Val Asp Thr Trp Arg
    610                 615

<210> SEQ ID NO 4
<211> LENGTH: 640
<212> TYPE: PRT
<213> ORGANISM: Aspergillus kawachi
```

<400> SEQUENCE: 4

```
Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Asn Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Glu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
            245                 250                 255

Pro Ala Leu Asp Cys Pro Tyr Gln Lys Tyr Leu Asp Gly Val Leu Asn
        260                 265                 270

Tyr Pro Ile Tyr Trp Gln Leu Leu Tyr Ala Phe Glu Ser Ser Ser Gly
    275                 280                 285

Ser Ile Ser Asn Leu Tyr Asn Met Ile Lys Ser Val Ala Ser Asp Cys
290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
            325                 330                 335

Ser Tyr Ile Phe Leu Ser Asp Gly Ile Pro Ile Val Tyr Ala Gly Glu
        340                 345                 350

Glu Gln His Tyr Ser Gly Gly Asp Val Pro Tyr Asn Arg Glu Ala Thr
    355                 360                 365

Trp Leu Ser Gly Tyr Asp Thr Ser Ala Glu Leu Tyr Thr Trp Ile Ala
370                 375                 380

Thr Thr Asn Ala Ile Arg Lys Leu Ala Ile Ser Ala Asp Ser Asp Tyr
385                 390                 395                 400

Ile Thr Tyr Ala Asn Asp Pro Ile Tyr Thr Asp Ser Asn Thr Ile Ala
            405                 410                 415
```

Met Arg Lys Gly Thr Ser Gly Ser Gln Ile Ile Thr Val Leu Ser Asn
                420                 425                 430

Lys Gly Ser Ser Gly Ser Ser Tyr Thr Leu Thr Leu Ser Gly Ser Gly
            435                 440                 445

Thr Tyr Ser Gly Thr Lys Leu Ile Glu Ala Tyr Thr Cys Thr Ser Val
        450                 455                 460

Thr Val Asp Ser Asn Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Asn Thr Thr Thr Thr Thr Ala Ala Thr Ser Thr
                500                 505                 510

Ser Lys Ala Thr Thr Ser Ser Ser Ser Ser Ala Ala Ala Thr Thr
            515                 520                 525

Ser Ser Ser Cys Thr Ala Thr Ser Thr Thr Leu Pro Ile Thr Phe Glu
530                 535                 540

Glu Leu Val Thr Thr Thr Tyr Gly Glu Glu Val Tyr Leu Ser Gly Ser
545                 550                 555                 560

Ile Ser Gln Leu Gly Glu Trp Asp Thr Ser Asp Ala Val Lys Leu Ser
                565                 570                 575

Ala Asp Asp Tyr Thr Ser Ser Asn Pro Glu Trp Ser Val Thr Val Ser
                580                 585                 590

Leu Pro Val Gly Thr Thr Phe Glu Tyr Lys Phe Ile Lys Val Asp Glu
                595                 600                 605

Gly Gly Ser Val Thr Trp Glu Ser Asp Pro Asn Arg Glu Tyr Thr Val
            610                 615                 620

Pro Glu Cys Gly Ser Gly Ser Gly Glu Thr Val Val Asp Thr Trp Arg
625                 630                 635                 640

<210> SEQ ID NO 5
<211> LENGTH: 10991
<212> TYPE: DNA
<213> ORGANISM: Artificial Sequence
<220> FEATURE:
<223> OTHER INFORMATION: constructed pTrex3g_Akalpha plasmid
<220> FEATURE:
<221> NAME/KEY: misc_feature
<222> LOCATION: (6562)..(6565)
<223> OTHER INFORMATION: n = inosine
<220> FEATURE:
<221> NAME/KEY: misc_feature
<222> LOCATION: (8869)..(8872)
<223> OTHER INFORMATION: n = inosine

<400> SEQUENCE: 5
ctgcagccac ttgcagtccc gtggaattct cacggtgaat gtaggccttt tgtagggtag      60
gaattgtcac tcaagcaccc ccaacctcca ttacgcctcc cccatagagt tcccaatcag     120
tgagtcatgg cactgttctc aaatagattg gggagaagtt gacttccgcc cagagctgaa     180
ggtcgcacaa ccgcatgata tagggtcggc aacggcaaaa aagcacgtgg ctcaccgaaa     240
agcaagatgt ttgcgatcta acatccagga acctggatac atccatcatc acgcacgacc     300
actttgatct gctggtaaac tcgtattcgc cctaaaccga agtgcgtggt aaatctacac     360
gtgggcccct ttcggtatac tgcgtgtgtc ttctctaggt gccattcttt ttcccttcct     420
ctagtgttga attgtttgtg ttggagtccg agctgtaact acctctgaat ctctggagaa     480
tggtggacta acgactaccg tgcacctgca tcatgtatat aatagtgatc ctgagaaggg     540

| | |
|---|---|
| gggtttggag caatgtggga ctttgatggt catcaaacaa agaacgaaga cgcctctttt | 600 |
| gcaaagtttt gtttcggcta cggtgaagaa ctggatactt gttgtgtctt ctgtgtattt | 660 |
| ttgtggcaac aagaggccag agacaatcta ttcaaacacc aagcttgctc ttttgagcta | 720 |
| caagaacctg tggggtatat atctagagtt gtgaagtcgg taatcccgct gtatagtaat | 780 |
| acgagtcgca tctaaatact ccgaagctgc tgcgaacccg gagaatcgag atgtgctgga | 840 |
| aagcttctag cgagcggcta aattagcatg aaaggctatg agaaattctg gagacggctt | 900 |
| gttgaatcat ggcgttccat tcttcgacaa gcaaagcgtt ccgtcgcagt agcaggcact | 960 |
| cattcccgaa aaaactcgga gattcctaag tagcgatgga accggaataa tataataggc | 1020 |
| aatacattga gttgcctcga cggttgcaat gcaggggtac tgagcttgga cataactgtt | 1080 |
| ccgtacccca cctcttctca acctttggcg tttccctgat tcagcgtacc cgtacaagtc | 1140 |
| gtaatcacta ttaacccaga ctgaccggac gtgttttgcc cttcatttgg agaaataatg | 1200 |
| tcattgcgat gtgtaatttg cctgcttgac cgactgggc tgttcgaagc ccgaatgtag | 1260 |
| gattgttatc cgaactctgc tcgtagaggc atgttgtgaa tctgtgtcgg gcaggacacg | 1320 |
| cctcgaaggt tcacggcaag ggaaaccacc gatagcagtg tctagtagca acctgtaaag | 1380 |
| ccgcaatgca gcatcactgg aaaatacaaa ccaatggcta aaagtacata agttaatgcc | 1440 |
| taaagaagtc atataccagc ggctaataat tgtacaatca agtggctaaa cgtaccgtaa | 1500 |
| tttgccaacg gcttgtgggg ttgcagaagc aacggcaaag ccccacttcc ccacgtttgt | 1560 |
| ttcttcactc agtccaatct cagctggtga tcccccaatt gggtcgcttg tttgttccgg | 1620 |
| tgaagtgaaa gaagacagag gtaagaatgt ctgactcgga gcgttttgca tacaaccaag | 1680 |
| ggcagtgatg gaagacagtg aaatgttgac attcaaggag tatttagcca gggatgcttg | 1740 |
| agtgtatcgt gtaaggaggt ttgtctgccg atacgacgaa tactgtatag tcacttctga | 1800 |
| tgaagtggtc catattgaaa tgtaagtcgg cactgaacag gcaaaagatt gagttgaaac | 1860 |
| tgcctaagat ctcgggccct cgggccttcg gcctttgggt gtacatgttt gtgctccggg | 1920 |
| caaatgcaaa gtgtggtagg atcgaacaca ctgctgcctt taccaagcag ctgagggtat | 1980 |
| gtgataggca aatgttcagg ggccactgca tggtttcgaa tagaaagaga agcttagcca | 2040 |
| agaacaatag ccgataaaga tagcctcatt aaacggaatg agctagtagg caaagtcagc | 2100 |
| gaatgtgtat atataaaggt tcgaggtccg tgcctccctc atgctctccc catctactca | 2160 |
| tcaactcaga tcctccagga gacttgtaca ccatcttttg aggcacagaa acccaatagt | 2220 |
| caaccatcac aagtttgtac aaaaaagcag gctccgcggc cgccccttc accatgagag | 2280 |
| tgtcgacttc aagtattgcc cttgctgtgt cccttttttgg gaagctggcc cttgggctgt | 2340 |
| cagctgcaga atggcgcact caatccatct acttcctttt gacggatcgg ttcggtagga | 2400 |
| cggacaattc gactacagct acgtgcaata ggggtgacca agtatggtat tgctgtactt | 2460 |
| ccgtcattca tctgctgact tggatagatc tactgtggtg gaagttggca aggaattatc | 2520 |
| aaccatgttc gtatctcact tcataccatc catgctgggc gcttctgact attgctccag | 2580 |
| ctggactata tccacggcat gggattcaca gctatctgga tctcgcctat cactgagcag | 2640 |
| ctaccccagg atacttcgga tggtgaagcc taccatggat actggcagca gaagatgtat | 2700 |
| gccctcattg cattcatatt ttatgcttac tcgcagactg cagctgactt ggcagataca | 2760 |
| atgtgaactc caacttcggc acggcagatg atctgaagtc cctctccgat gctcttcacg | 2820 |
| cccgcggaat gtacctcatg gtcgacgtcg tccctaacca catggtaagt actgctttac | 2880 |
| ctctatatta gtaaacccaa tgcgaacaat gactgtatca gggctacgca ggtaacggca | 2940 |

```
acgatgtgga ttacagcgtc ttcgacccct tcgactcctc ctcctacttc catccatact   3000
gcctcatcac agattgggac aacttgacca tggtccaaga ctgttgggag ggtgacacca   3060
tcgtgtctct gccagatctg aacaccacgg aaaccgccgt gagaaccatt tggtacgatt   3120
gggtagccga cctggtatcc aactactcag gtgcgacccc aacccactaa acaagccac    3180 atactaaaaa attgctcagt cgacggcctc cgtatcgaca gtgtcgaaga agtcgaaccc   3240
gacttcttcc cgggctacca agaagcagca ggagtctact gcgtcggtga agtcgacaac   3300
ggcaaccctg ctctcgactg cccataccaa aaatatctag atggtgttct caactatccc   3360
atgtacatac ccccttctac cttctcgaac ccatcactaa ctcaattgct gcagctactg   3420
gcaactcctc tacgcctttg aatcctccag cggcagcatc agcaacctct acaacatgat   3480
caaatccgtc gccagcgact gctccgatcc gaccctcctg ggcaacttta tcgaaaacca   3540
cgacaacccc cgcttcgcct cgtatgtccc ttccatcact gcccccttt aaagtaaacc    3600 ccactgacag gcaaagctac acatccgact actcccaagc caaaaacgtc ctcagctaca   3660
tcttcctctc cgacggcatc cccatcgtct acgccggcga agaacagcac tactccggcg   3720
gcgacgtgcc ctacaaccgc gaagctacct ggctatcagg ctacgacacc tccgcggagc   3780
tctacacctg gatagccacc acaaacgcga tccggaaact agctatctca gcagactcgg   3840
actacattac ttacgcggtt tgcccttttcc cttcccccca cccagagctc aaccccatt    3900 ctaacaaaat atttcaatgg tagaacgacc caatctacac agacagcaac accatcgcga   3960
tgcgcaaagg cacctccggc tcccaaatca tcaccgtcct ctccaacaaa ggctcctccg   4020
gaagcagcta caccctcacc ctcagcggaa gcggctacac gtccggcacg aagctcatcg   4080
aagcgtacac ctgcacgtcc gtgacggtgg actcgaacgg ggatatccct gtgccgatgg   4140
cttcgggatt acctagagtt ctcctccctg cttcggtggt tgatagttct tcgctttgtg   4200
gggggagtgg taacacaacc acgaccacaa ctgctgctac ctccacatcc aaagccacca   4260
cctcctcttc ttcttcttct gctgctgcta ctacttcttc atcatgcacc gcaacaagca   4320
ccaccctccc catcaccttc gaagaactcg tcaccactac ctacgggaa gaagtctacc    4380 tcagcggatc tatctcccag ctcggagagt gggatacgag tgacgcggtg aagttgtccg   4440
cggatgatta tacctcgagt aaccccgagt ggtctgttac tgtgtcgttg ccggtgggga   4500
cgaccttcga gtataagttt attaaggtcg atgagggtgg aagtgtgact tgggaaagtg   4560
atccgaatag ggagtatact gtgcctgaat gtgggagtgg gagtgggag acggtggttg    4620 atacgtggag gtagaagggt gggcgcgccg acccagcttt cttgtacaaa gtggtgatcg   4680
cgccagctcc gtgcgaaagc ctgacgcacc ggtagattct tggtgagccc gtatcatgac   4740
ggcggcggga gctacatggc cccgggtgat ttatttttt tgtatctact tctgacccctt   4800 ttcaaatata cggtcaactc atctttcact ggagatgcgg cctgcttggt attgcgatgt   4860
tgtcagcttg gcaaattgtg gctttcgaaa acacaaaacg attccttagt agccatgcat   4920
ttttaagata acggaataga agaaagagga aattaaaaaa aaaaaaaaaa caaacatccc   4980
gttcataacc cgtagaatcg ccgctcttcg tgtatcccag taccagttta ttttgaatag   5040
ctcgcccgct ggagagcatc ctgaatgcaa gtaacaaccg tagaggctga cacggcaggt   5100
gttgctaggg agcgtcgtgt tctacaaggc cagacgtctt cgcggttgat atatatgtat   5160
gtttgactgc aggctgctca gcgacgcacg tcaagttcgc cctcgctgct tgtgcaataa   5220
tcgcagtggg gaagccacac cgtgactccc atctttcagt aaagctctgt tggtgtttat   5280
```

```
cagcaataca cgtaatttaa actcgttagc atggggctga tagcttaatt accgtttacc   5340
agtgccatgg ttctgcagct ttccttggcc cgtaaaattc ggcgaagcca gccaatcacc   5400
agctaggcac cagctaaacc ctataattag tctcttatca acaccatccg ctcccccggg   5460
atcaatgagg agaatgaggg ggatgcgggg ctaaagaagc ctacataacc ctcatgccaa   5520
ctcccagttt acactcgtcg agccaacatc ctgactataa gctaacacag aatgcctcaa   5580
tcctgggaag aactggccgc tgataagcgc gcccgccctc gcaaaaacca tccctgatga   5640
atggaaagtc cagacgctgc ctgcggaaga cagcgttatt gatttcccaa agaaatcggg   5700
gatcctttca gaggccgaac tgaagatcac agaggcctcc gctgcagatc ttgtgtccaa   5760
gctggcggcc ggagagttga cctcggtgga agttacgcta gcattctgta acgggcagc    5820 aatcgcccag cagttagtag ggtcccctct acctctcagg gagatgtaac aacgccacct   5880
tatgggacta tcaagctgac gctggcttct gtgcagacaa actgcgccca cgagttcttc   5940
cctgacgccg ctctcgcgca ggcaagggaa ctcgatgaat actacgcaaa gcacaagaga   6000
cccgttggtc cactccatgg cctcccatc tctctcaaag accagcttcg agtcaaggta    6060
caccgttgcc cctaagtcgt tagatgtccc tttttgtcag ctaacatatg ccaccagggc   6120
tacgaaacat caatgggcta catctcatgg ctaaacaagt acgacgaagg ggactcggtt   6180
ctgacaacca tgctccgcaa agccggtgcc gtcttctacg tcaagacctc tgtcccgcag   6240
accctgatgg tctgcgagac agtcaacaac atcatcgggc gcaccgtcaa cccacgcaac   6300
aagaactggt cgtgcggcgg cagttctggt ggtgagggtg cgatcgttgg gattcgtggt   6360
ggcgtcatcg gtgtaggaac ggatatcggt ggctcgattc gagtgccggc cgcgttcaac   6420
ttcctgtacg gtctaaggcc gagtcatggg cggctgccgt atgcaaagat ggcgaacagc   6480
atggagggtc aggagacggt gcacagcgtt gtcgggccga ttacgcactc tgttgagggt   6540
gagtccttcg cctcttcctt cnnnncctgc tctataccag gcctccactg tcctcctttc   6600
ttgcttttta tactatatac gagaccggca gtcactgatg aagtatgtta gacctccgcc   6660
tcttcaccaa atccgtcctc ggtcaggagc catggaaata cgactccaag gtcatcccca   6720
tgccctggcg ccagtccgag tcggacatta ttgcctccaa gatcaagaac ggcgggctca   6780
atatcggcta ctacaacttc gacggcaatg tccttccaca ccctcctatc ctgcgcggcg   6840
tggaaaccac cgtcgccgca ctcgccaaag ccggtcacac cgtgaccccg tggacgccat   6900
acaagcacga tttcggccac gatctcatct cccatatcta cgcggctgac ggcagcgccg   6960
acgtaatgcg cgatatcagt gcatccggcg agccggcgat tccaaatatc aaagacctac   7020
tgaacccgaa catcaaagct gttaacatga acgagctctg ggacacgcat ctccagaagt   7080
ggaattacca gatggagtac cttgagaaat ggcgggaggc tgaagaaaag gccgggaagg   7140
aactggacgc catcatcgcg ccgattacgc ctaccgctgc ggtacggcat gaccagttcc   7200
ggtactatgg gtatgcctct gtgatcaacc tgctggattt cacgagcgtg gttgttccgg   7260
ttacctttgc ggataagaac atcgataaga agaatgagag tttcaaggcg gttagtgagc   7320
ttgatgccct cgtgcaggaa gagtatgatc cggaggcgta ccatgggca ccggttgcag    7380 tgcaggttat cggacggaga ctcagtgaag agaggacgtt ggcgattgca gaggaagtgg   7440
ggaagttgct gggaaatgtg gtgactccat agctaataag tgtcagatag caatttgcac   7500
aagaaatcaa taccagcaac tgtaaataag cgctgaagtg accatgccat gctacgaaag   7560
agcagaaaaa aacctgccgt agaaccgaag agatatgaca cgcttccatc tctcaaagga   7620 agaatcccgtt cagggttgcg tttccagtct agacacgtat aacggcacaa gtgtctctca   7680
```

```
ccaaatgggt tatatctcaa atgtgatcta aggatggaaa gcccagaata tcgatcgcgc   7740
gcagatccat atatagggcc cgggttataa ttacctcagg tcgacgtccc atggccattc   7800
gaattcgtaa tcatggtcat agctgttttcc tgtgtgaaat tgttatccgc tcacaattcc   7860
acacaacata cgagccggaa gcataaagtg taaagcctgg ggtgcctaat gagtgagcta   7920
actcacatta ttgcgttgc gctcactgcc cgctttccag tcgggaaacc tgtcgtgcca   7980
gctgcattaa tgaatcggcc aacgcgcggg gagaggcggt ttgcgtattg ggcgctcttc   8040
cgcttcctcg ctcactgact cgctgcgctc ggtcgttcgg ctgcggcgag cggtatcagc   8100
tcactcaaag gcggtaatac ggttatccac agaatcaggg gataacgcag gaaagaacat   8160
gtgagcaaaa ggccagcaaa aggccaggaa ccgtaaaaag gccgcgttgc tggcgttttt   8220
ccataggctc cgcccccctg acgagcatca caaaaatcga cgctcaagtc agaggtggcg   8280
aaacccgaca ggactataaa gataccaggc gtttccccct ggaagctccc tcgtgcgctc   8340
tcctgttccg accctgccgc ttaccggata cctgtccgcc tttctccctt cgggaagcgt   8400
ggcgctttct catagctcac gctgtaggta tctcagttcg gtgtaggtcg ttcgctccaa   8460
gctgggctgt gtgcacgaac ccccgttca gcccgaccgc tgcgccttat ccggtaacta   8520
tcgtcttgag tccaacccgg taagacacga cttatcgcca ctggcagcag ccactggtaa   8580
caggattagc agagcgaggt atgtaggcgg tgctacagag ttcttgaagt ggtggcctaa   8640
ctacggctac actagaagaa cagtatttgg tatctgcgct ctgctgaagc cagttacctt   8700
cggaaaaaga gttggtagct cttgatccgg caaacaaacc accgctggta gcggtggttt   8760
ttttgtttgc aagcagcaga ttacgcgcag aaaaaaagga tctcaagaag atccmgatct   8820
tttctacggg gtctgacgct cagtggaacg aaaactcacg ttaagggann nnggtcatga   8880
gattatcaaa aaggatcttc acctagatcc ttttaaatta aaaatgaagt tttaaatcaa   8940
tctaaagtat atatgagtaa acttggtctg acagttacca atgcttaatc agtgaggcac   9000
ctatctcagc gatctgtcta tttcgttcat tcatagttgc ctgactcccc gtcgtgtaga   9060
taactacgat acgggagggc ttaccatctg gccccagtgc tgcaatgata ccgcgagacc   9120
cacgctcacc ggctccagat ttatcagcaa taaaccagcc agccggaagg gccgagcgca   9180
gaagtggtcc tgcaacttta tccgcctcca tccagtctat taattgttgc cgggaagcta   9240
gagtaagtag ttcgccagtt aatagtttgc gcaacgttgt tgccattgct acaggcatcg   9300
tggtgtcacg ctcgtcgttt ggtatggctt cattcagctc cggttcccaa cgatcaaggc   9360
gagttacatg atccccccatg ttgtgcaaaa aagcggttag ctccttcggt cctccgatcg   9420
ttgtcagaag taagttggcc gcagtgttat cactcatggt tatggcagca ctgcataatt   9480
ctcttactgt catgccatcc gtaagatgct tttctgtgac tggtgagtac tcaaccaagt   9540
cattctgaga atagtgtatg cggcgaccga gttgctcttg cccggcgtca atacgggata   9600
ataccgcgcc acatagcaga actttaaaag tgctcatcat tggaaaacgt tcttcggggc   9660
gaaaactctc aaggatctta ccgctgttga gatccagttc gatgtaaccc actcgtgcac   9720
ccaactgatc ttcagcatct tttactttca ccagcgtttc tgggtgagca aaaacaggaa   9780
ggcaaaatgc cgcaaaaaag gaataagggc gacacggaa atgttgaata ctcatactct   9840
tcctttttca atattattga agcatttatc agggttattg tctcatgagc ggatacatat   9900
ttgaatgtat ttagaaaaat aaacaaatag gggttccgcg cacatttccc cgaaaagtgc   9960
cacctgacgt ctaagaaacc attattatca tgacattaac ctataaaaat aggcgtatca   10020
```

```
cgaggccctt tcgtctcgcg cgtttcggtg atgacggtga aaacctctga cacatgcagc    10080
tcccggagac ggtcacagct tgtctgtaag cggatgccgg gagcagacaa gcccgtcagg    10140
gcgcgtcagc gggtgttggc gggtgtcggg gctggcttaa ctatgcggca tcagagcaga    10200
ttgtactgag agtgcaccat aaaattgtaa acgttaatat tttgttaaaa ttcgcgttaa    10260
atttttgtta aatcagctca tttttaacc aataggccga aatcggcaaa atcccttata    10320
aatcaaaaga atagcccgag ataggttga gtgttgttcc agtttggaac aagagtccac    10380
tattaaagaa cgtggactcc aacgtcaaag ggcgaaaaac cgtctatcag ggcgatggcc    10440
cactacgtga accatcaccc aaatcaagtt ttttggggtc gaggtgccgt aaagcactaa    10500
atcggaaccc taaagggagc ccccgattta gagcttgacg gggaaagccg gcgaacgtgg    10560
cgagaaagga agggaagaaa gcgaaaggag cgggcgctag ggcgctggca agtgtagcgg    10620
tcacgctgcg cgtaaccacc acacccgccg cgcttaatgc gccgctacag ggcgcgtact    10680
atggttgctt tgacgtatgc ggtgtgaaat accgcacaga tgcgtaagga gaaaataccg    10740
catcaggcgc cattcgccat tcaggctgcg caactgttgg gaagggcgat cggtgcgggc    10800
ctcttcgcta ttacgccagc tggcgaaagg gggatgtgct gcaaggcgat taagttgggt    10860
aacgccaggg ttttcccagt cacgacgttg taaaacgacg gccagtgccc aagcttacta    10920
gtacttctcg agctctgtac atgtccggtc gcgacgtacg cgtatcgatg gcgccagctg    10980
caggcggccg c                                                          10991

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
caccatgaga gtgtcgactt caag                                                24

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ctacctccac gtatcaacca c                                                   21
```

HETEROLOGOUS EXPRESSION OF AN *ASPERGILLUS KAWACHI* ACID-STABLE ALPHA AMYLASE AND APPLICATIONS IN GRANULAR STARCH HYDROLYSIS

The present application claims priority to U.S. Provisional Patent Application Ser. No. 60/575,175, entitled Heterologous Expression of an *Aspergillus kawachi* Acid-Stable Alpha Amylase and Applications in Granular Starch Hydrolysis, filed May 27, 2004 and U.S. Provisional Patent Application Ser. No. 60/605,437, entitled Heterologous Expression of an *Aspergillus kawachi* Acid-Stable Alpha Amylase and Applications in Granular Starch Hydrolysis, filed Aug. 30, 2004.

FIELD OF THE INVENTION

The present invention relates to an acid-stable alpha amylase (asAA) derived from a strain of *Aspergillus kawachi*, which has granular starch hydrolyzing (GSH) activity. Further the invention relates to the heterologous expression of an asAA having GSH activity in filamentous fungal host cells and particularly in *Trichoderma* and *Aspergillus* cells and the use of asAA having GSH activity in compositions, which optionally include glucoamylases, to enhance starch hydrolysis and alcohol production.

BACKGROUND OF THE INVENTION

Glucoamylases, and particularly glucoamylases having granular starch hydrolyzing (GSH) activity are important industrial enzymes used for producing products such as organic acids (i.e. lactic acids), amino acids (i.e. glutamic acids), alcohols (i.e. ethanol) and other compounds from starch substrates derived from grains and cereals. During microbial fermentations, and particularly during simultaneous saccharification and fermentation (SSF), it would be of benefit to reduce the amount of residual starch in the fermentation when granular starch substrates are used as a carbon feed. The present invention answers this need by providing an acid-stable alpha amylase (asAA) having granular starch hydrolyzing activity, which may be used in combination with a glucoamylase to enhance starch hydrolysis and alcohol production.

Additionally, benefits of the present invention over prior art compositions and methods include one or more of the following: a) a reduction of thermal energy use during starch hydrolysis and end-product production; b) reduction in the requirement of high enzyme dosage; c) utilization of a continuous internal glucose feed; d) maintenance of a relatively low glucose level in the fermenter, which significantly reduces the high risk of microbial contamination and removes the catabolite repression of yeast due to high concentration of free glucose; e) reduction in formation of browning reaction products; f) reduction or removal of calcium addition, which was required during the prior art jet cooking process; g) reduction in water utilization during the fermentation process; h) use of higher solids content in the fermentation, which may result in higher end-product formation and reduced energy costs; i) reduced levels of production of certain by-products, such as glycerol; and j) decreased residual starch content of distillers dry grains plus solubles.

SUMMARY OF THE INVENTION

In one aspect, the invention relates to a method for producing an alcohol which comprises contacting a granular starch substrate with an acid-stable alpha amylase (asAA) having granular starch hydrolyzing (GSH) activity and a glucoamylase (GA) in a fermentation step which further comprises ethanologenic microorganisms and producing an alcohol in the fermentation step. In some embodiments, the granular starch substrate is obtained from corn or wheat. In other embodiments, the asAA having GSH activity is obtained from the expression of a heterologous polynucleotide in a fungal host cell which encodes an asAA having at least 90% sequence identity to the sequence of SEQ ID NO: 3. In one preferred embodiment, the fermentation step includes the fungal cells which express the asAA and in other embodiments the fermentation step includes a cell free asAA extract. In further embodiments, the fungal host cell is a *Trichoderma* cell. In other embodiments the alcohol, which is produced by the method is ethanol and the ethanologenic microorganism is a yeast. In additional embodiments, the GA is produced from the expression of a heterologous polynucleotide in a fungal host. In yet other embodiments, the alcohol is recovered from the fermentation.

In a second aspect, the invention relates to a fungal host cell comprising a heterologous polynucleotide that encodes an acid-stable alpha amylase (asAA) having granular starch hydrolyzing (GSH) activity which has at least 90% sequence identity to the sequence of SEQ ID NO: 3, and in some embodiments the heterologous polynucleotide will encode an asAA having GSH activity with at least 95% sequence identity to the sequence of SEQ ID NO: 3. In some embodiments, the asAA having GSH activity which is expressed from the fungal host has a lower pH optimum than an asAA having GSH activity obtained from a native host. In one embodiment, the fungal host cell is a *Trichoderma* cell. In a further embodiment, the *Trichoderma* host cell is a *T. reesei* cell. In another embodiment, the fungal host cell is an *Aspergillus* cell.

In a third aspect, the invention relates to a granular starch hydrolyzing enzyme composition which comprises an acid-stable alpha amylase (asAA) having granular starch hydrolyzing (GSH) activity, wherein the asAA having GSH activity has at least 90% sequence identity to the sequence of SEQ ID NO: 3. In some embodiments, the asAA will be obtained from the expression of a heterologous polynucleotide in a fungal host cell. In further embodiments, the fungal host cell will be a *Trichoderma* or *Aspergillus* host cell. In other embodiments, the composition will further include a glucoamylase enzyme. In some preferred embodiments, the glucoamylase enzyme will be obtained from a strain of *Aspergillus* or *Rhizopus*. In other embodiments, the glucoamylase will be a glucoamylase having GSH activity and will be obtained from a strain of *Aspergillus, Rhizopus* or *Humicola*. In other embodiments, both the asAA and the glucoamylase will be expressed in a fungal host having a heterologous polynucleotide which expresses an asAA having GSH activity and a glucoamylase. In some embodiments, the fungal host strain will be the same and in other embodiments, the fungal host strain will be different strains. In other embodiments, the invention relates to a method of hydrolyzing granular starch using the enzyme composition of this aspect.

In a fourth aspect, the invention relates to a method of increasing the granular starch hydrolyzing activity of a composition comprising a glucoamylase, which comprises adding an acid-stable alpha amylase (asAA) having granular starch hydrolyzing (GSH) activity to a composition which includes a granular starch substrate and a glucoamylase to produce a soluble starch hydrolysate wherein the asAA having GSH activity has an amino acid sequence of at least 90% sequence identity to SEQ DI NO: 3 and the amount of solubilized starch is greater than a corresponding composition absent the asAA having GSH activity.

In a fifth aspect, the invention relates to a one-step method for producing an alcohol, preferably ethanol, from a grain substrate comprising mixing in a fermentation medium under suitable fermentation conditions (i) a granular starch substrate derived from a grain, (ii) an acid-stable alpha amylase (asAA) having granular starch hydrolyzing activity, and (iii) ethanologenic microorganisms to obtain a fermented composition including an alcohol. In one embodiment, the asAA having GSH activity has at least 90% sequence identity to the sequence of SEQ ID NO: 3. In another embodiment, the asAA having GSH activity is obtained from expression in a *Trichoderma* host. In a further embodiment, a glucoamylase is added to the step. In yet another embodiment, the invention relates to the fermentated composition obtained according to this method. In another embodiment, the ethanol produced according to the method encompassed by the invention is recovered. In other embodiments, the grain is obtained from corn, wheat, barely, potatoes, rice, sorghum or tapioca.

In a sixth aspect, the invention relates to a method for reducing the amount of residual starch in distillers' dried grains plus solids (DDGS) comprising producing an alcohol by a method of the invention, distilling the alcohol to obtain a fermentation residue, and treating the fermentation residue to obtain distillers dried grain with solubles.

BRIEF DESCRIPTION OF THE DRAWINGS

FIG. 1 provides the genomic DNA sequence coding for the native *Aspergillus kawachi* acid-stable alpha-amylase, which is designated asaA (SEQ ID NO:1). The eight putative introns are underlined.

FIG. 2 provides the signal sequence (SEQ ID NO: 2) and mature amino acid sequence (SEQ ID NO: 3) (AsaA) for *A. kawachi* acid stable alpha-amylase (SEQ ID NO: 4). The putative signal sequence (amino acids 1–21) is underlined and bold.

FIGS. 3A–D provide the complete nucleotide sequence (SEQ ID NO: 5), 10990 bp, of plasmid pTrex3g_Akalpha (FIG. 4).

DETAILED DESCRIPTION OF THE INVENTION

Figure 4:
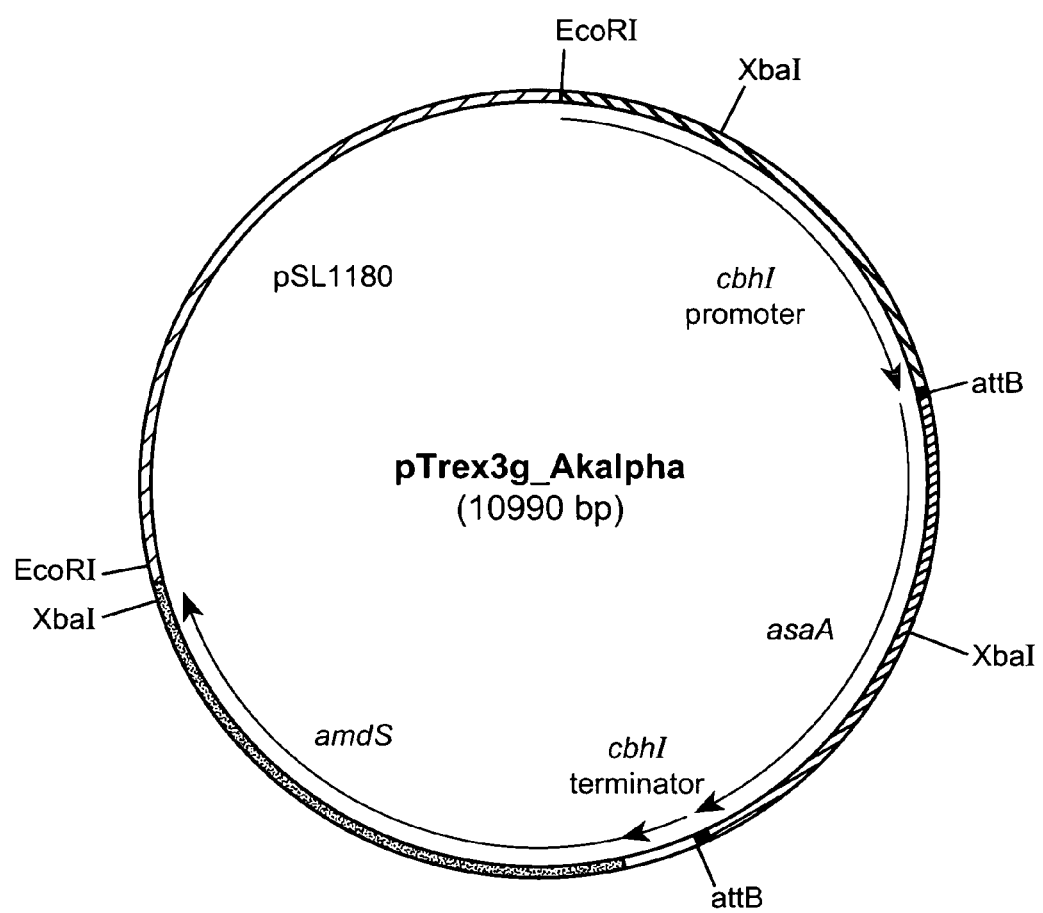
FIG. 4 provides a map of pTrex3g_Akalpha, which was used for expression of the nucleic acid encoding the AsaA (*Aspergillus kawachi* asAA) and which contains EcoRI sites flanking the fungal expression vector, wherein
   a) cbhl promoter is the *Trichoderma reesei* cellobiohydrolase promoter;
   b) asaA is the *Aspergillus kawachi* polynucleotide encoding the acid stable alpha amylase of SEQ ID NO. 4;
   c) cbhl terminator is the *Trichoderma reesei* cellobiohydrolase terminator;
   d) amdS is an *Aspergillus nidulans* acetamidase nutritional marker gene; and
   e) attB is a Gateway cloning system (Invitrogen) lambda phage site for recombination.

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTO- COLS IN MOLECULAR BIOLOGY (1994). These general references provide definitions and methods known to those in the art. However, it is not intended that the present invention be limited to any particular methods, protocols, and reagents described, as these may vary.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, NY (1991) provide one of skill with general dictionaries of many of the terms used in this invention.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole.

A. Definitions

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

The term "granular starch" refers to raw (uncooked) starch, e.g., granular starch that has not been subject to gelatinization.

The terms "granular starch hydrolyzing (GSH) enzyme" or "having granular starch hydrolyzing (GSH) activity" refer to enzymes, which have the ability to hydrolyze starch in granular form.

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

The term "acid-stable alpha amylase ("asAA")" refers to an alpha amylase that is active in the pH. range of pH 3.0 to 7.0 and preferably 3.5 to 6.0.

The term "glucoamylase" refers to the amyloglucosidase class of enzymes (e.g., EC.3.2.1.3, glucoamylase, 1,4-alpha-O-glucan glucohydrolase). These are exo-acting enzymes, which release glucosyl residues from the non-reducing ends of amylose and amylopectin molecules. The enzyme also hydrolyzes alpha-1,6 and alpha-1,3 linkages although at much slower rate than alpha-1,4 linkages.

The term "glycosylation" refers to the post-transcriptional modification of a protein by the addition of carbohydrate moieties, wherein the carbohydrate is either N-linked or O-linked resulting in a glucoprotein. An N-linked carbohydrate moiety of a glycoprotein is attached by a glycosidic bond to the β-amide nitrogen of an asparagine residue. An O-linked carbohydrate is attached by a glycosidic bond to a protein through the hydroxy group of a serine or a threonine residue.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "protein" and "polypeptide" are used interchangeably herein. The conventional one-letter or three-letter code for amino acid residues is used herein.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

The term "native acid-stable alpha amylase (n-asAA)" refers to an asAA produced from the endogenous expression of the asAA. For example, the term "n-asaA" means the endogenous expression of an acid-stable alpha amylase (i e, SEQ ID NO: 3) from an *Aspergillus kawachi*.

The terms "recombinant acid-stable alpha amylase (r-asAA)", "recombinantly expressed asAA" and "recombinantly produced asAA" refer to a mature asAA protein sequence that is produced in a host cell from the expression of a heterologous polynucleotide. For example, the term "r-asaA" means the *Aspergillus kawachi* acid-stable alpha amylase (i.e., SEQ ID NO: 3) is expressed and produced in a host in which a polynucleotide encoding the asaA has been introduced. The mature protein sequence of a r-asAA excludes a signal sequence.

A "gene" refers to a DNA segment that is involved in producing a polypeptide and includes regions preceding and following the coding regions as well as intervening sequences (introns) between individual coding segments (exons).

The term "nucleic acid" encompasses DNA, nRNA, single stranded or double stranded and chemical modifications thereof. The terms "nucleic acid" and "polynucleotide" may be used interchangeably herein. Because the genetic code is degenerate, more than one codon may be used to encode a particular amino acid, and the present invention encompasses polynucleotides, which encode a particular amino acid sequence.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. A preferred promoter used in the invention is *Trichoderma reesei* cbh1, which is an inducible promoter.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein when describing proteins and genes that encode them, the term for the gene is italicized, (e.g., the gene that encodes asaA (*A. kawachi* asAA) may be denoted as *asaA*). The term for the protein is generally not italicized and the first letter is generally capitalized, (e.g., the protein encoded by the *asaA* gene may be denoted as AsaA or asaA).

The term "derived" encompasses the terms "originated from", "obtained" or "obtainable from", and "isolated from".

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

A polynucleotide or a polypeptide having a certain percent (e.g. 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al., (eds) 1987, Supplement 30, section 7.7.18). Preferred programs include the GCG Pileup program, FASTA (Pearson et al. (1988) *Proc. Natl, Acad. Sci USA* 85:2444–2448), and BLAST (BLAST Manual, Altschul et al., Natl. Cent. Biotechnol. Inf., Natl Lib. Med. (NCIB NLM NIH), Bethesda, Md., and Altschul et al., (1997) *NAR* 25:3389–3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

One skilled in the art will recognize that sequences encompassed by the invention are also defined by the ability to hybridize under stringent hybridization conditions with the exemplified asaA sequence (e.g., SEQ ID NO:1). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1×SSC, 0.1% SDS.

"Host strain" or "host cell" means a suitable host for an expression vector or DNA construct comprising a polynucleotide encoding a granular starch hydrolyzing enzyme according to the invention. Specifically, host strains are preferably filamentous fungal cells. In a preferred embodiment of the invention, "host cell" means both the cells and protoplasts created from the cells of a filamentous fungal strain and particularly a *Trichoderma* sp. or an *Aspergillus* sp.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, (e.g., *Trichoderma reesei* (previously classified as *T. longibrachiatum* and currently also known as *Hypocrea jecorina*), *Trichoderma viride, Trichoderma koningii, Trichoderma harzianum*); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *A. oryzae, A. niger*, and *A. awamori*), *Fusarium* sp., *Neurospora* sp., *Hypocrea* sp., and *Emericella* sp. (See also, Innis et al., (1985) *Sci.* 228:21–26).

As used herein, the term "*Trichoderma*" or "*Trichoderma* sp." refer to any fungal genus previously or currently classified as *Trichoderma*.

The term "culturing" refers to growing a population of microbial cells under suitable conditions in a liquid or solid medium. In one embodiment, culturing refers to fermentative bioconversion of a starch substrate containing granular starch to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

The phrase "simultaneous saccharification and fermentation (SSF)" refers to a process in the production of biochemicals in which a microbial organism, such as an ethanol producing microorganism and at least one enzyme such as an asAA are in the same process step. In one embodiment of the present invention, SSF refers to the contemporaneous hydrolysis of granular starch substrates to saccharides including glucose and the fermentation of the saccharides into alcohol in the same reactor vessel.

The term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "enzymatic conversion" in general refers to the modification of a substrate by enzyme action. The term as used herein also refers to the modification of a granular starch substrate by the action of an enzyme.

As used herein the term "saccharification" refers to enzymatic conversion of starch to glucose.

The term "gelatinization" means solubilization of a starch molecule by cooking to form a viscous suspension.

The term "liquefaction" refers to the stage in starch conversion in which gelatinized starch is hydrolyzed to give low molecular weight soluble dextrins. The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

The terms "end-product" or "desired end-product" refer to any carbon-source derived molecule product which is enzymatically converted from the granular starch substrate.

As used herein the term "dry solids content (ds)" refers to the total solids of a slurry in % on a dry weight basis. The term "slurry" refers to an aqueous mixture containing insoluble solids.

The term "residual starch" refers to the remaining starch (soluble or insoluble) left in a composition after fermentation of a starch containing substrate.

As used herein "a recycling step" refers to the recycling of mash components, which may include residual starch, enzymes and/or microorganisms to ferment substrates comprising granular starch.

The term "mash" refers to a mixture of a fermentable carbon source (carbohydrate) in water used to produce a fermented product, such as an alcohol. In some embodiments, the term "beer" and "mash" are used interchangeability.

The term "stillage" means a mixture of non-fermented solids and water, which is the residue after removal of alcohol from a fermented mash.

The terms "distillers dried grain (DDG)" and "distillers dried grain with solubles (DDGS)" refer to a useful by-product of grain fermentation.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Sacchromyces*, particularly, *S. cerevisiae*.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes.

The term "endogenous" with reference to a polynucleotide or protein refers to a polynucleotide or protein that occurs naturally in the host cell.

The terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein the term "specific activity" means an enzyme unit defined as the number of moles of substrate converted to product by an enzyme preparation per unit time under specific conditions. Specific activity is expressed as units (U)/mg of protein.

As used herein the term "enzyme unit" refers to the amount of enzyme that produces 1 micromole of product per minute under the specified conditions of the assay.

For example, in one embodiment, the term "glucoamylase activity unit" (GAU) is defined as the amount of enzyme required to produce 1 g of glucose per hour from soluble starch substrate (4% ds) under assay conditions of 60° C. and pH 4.2.

In another embodiment, a granular starch hydrolyzing enzyme unit (GSHE U) is 6 defined as being the amount of GSHE required to produce 1 mg of glucose per minute from granular starch under assay conditions of, for example 25° C. at pH 5.0. In a preferred embodiment, a GSHE U is defined as being the amount of a GSHE required to produce 1 mg glucose/min from a granular starch substrate at 50° C. at pH 4.5. The term "yield"refers to the amount of end-product or desired end-products produced using the methods of the present invention. In some preferred embodiments, the yield is greater than that produced using methods known in the art. In some embodiments, the term refers to the volume of the end product and in other embodiment the term refers to the concentration of the end product.

"ATCC" refers to American Type Culture Collection located at Manassas, Va. 20108 (ATCC; <www.atcc.org>).

"NRRL" refers to the Agricultural Research Service Culture Collection, National Center for Agricultural Utilization Research (and previously known as USDA Northern Regional Research Laboratory), Peoria, ILL.

"A", "an" and "the" include plural references unless the context clearly dictates otherwise.

As used herein the term "comprising" and its cognates are used in their inclusive sense; that is, equivalent to the term "including" and its corresponding cognates.

B. Preferred Embodiments

The present invention relates to a granular starch hydrolyzing enzyme composition which comprises an acid-stable alpha amylase (asAA) having granular starch hydrolyzing (GSH) activity and optionally comprising a glucoamylase, wherein the asM has at least 90% sequence identity to the sequence of SEQ ID NO: 3. In certain preferred embodiments, the invention provides means for the production of desired end-products of the bioconversion of a granular starch substrate and in preferred embodiments, the asAA is contacted with a slurry of a granular starch substrate and the granular starch substrate is directly converted to an end-product without gelatinization and liquefaction of the granular starch substrate.

Granular Starch Substrates

A granular starch substrate to be processed in the methods of the invention may be obtained from any plant part including stems, grains, roots and tubers. Particularly preferred plant sources include corn; wheat; rye; sorghum; rice; millet; barley; cassava; legumes, such as beans and peas; potatoes; sweet potatoes; bananas; and tapioca.

Specifically contemplated starch substrates are cornstarch and wheat starch. The starch from a grain may be ground or whole and includes corn solids, such as kernels, bran and/or cobs. The starch may be highly refined raw starch or feedstock from starch refinery processes. Those of general skill in the art are well aware of available methods which may be used to prepare granular starch substrates for use in the methods encompassed by the invention. Some of these methods include dry milling of whole cereal grains using hammer mills and roller mills and wet milling.

Various starches are commercially available. For example, cornstarches are available from Cerestar, Sigma, and Katayama Chemical Industry Co. (Japan); wheat starches are available from Sigma; sweet potato starches are available from Wako Pure Chemical Industry Co. (Japan); and potato starch is available from Nakaari Chemical Pharmaceutical Co. (Japan).

Various references have reported on the amount of starch found in cereal grains and reference is made to The Alcohol Textbook, 3$^{rd}$ Ed. K. Jacques et al., Eds. 1999, Nottingham University Press. For example corn contains about 60–68% starch; barley contains about 55–65% starch; millet contains about 75–80% starch; wheat contains about 60–65% starch; and polished rice contains 70–72% starch.

In some embodiments of the method encompassed by the invention, the granular starch substrate is slurried (generally with water) and the slurry comprises i) about 10 to about 55% dry solids content (ds); ii) about 15 to about 50% dry solids content; iii) about 20 to about 45% dry solids content; iv) about 25 to about 45% dry solids content; v) about 30 to about 45% dry solids content; vi) about 30 to about 40% dry solids content; and also vii) about 30 to 35% dry solids content.

Acid-Stable Alpha Amylases (asAA) Having Granular Starch Hydrolyzing (GSH) Activity In one embodiment an asAA having GSH activity is obtained from a strain of *Aspergillus*, e.g., *A. oryzae*, *A. kawachi*, *A. niger*, and *A. awamori*.

In a particularly preferred embodiment, the asAA having GSH activity comprises an amino acid sequence having at least 80%, at least 85%, at least 90%, at least 93%, at least 94%, at least 95%, at least 96%, at least 97%, at least 98% and at least 99% sequence identity with the amino acid sequence set forth in SEQ ID NO: 3. In another embodiment, the asAA having GSH activity comprises an amino acid sequence having at least 90% sequence identity with SEQ ID NO: 3. In a further embodiment, the asAA having GSH activity comprises an amino acid sequence having at least 95% sequence identity to SEQ ID NO: 3. The asAA may also comprise an amino acid sequence having at least 98% sequence identity with SEQ ID NO: 3. In a further embodiment, the asAA having GSH activity comprises the amino acid sequence of SEQ ID NO: 3.

In other embodiments, the asM comprising the amino acid sequence of SEQ ID NO: 3 or an amino acid sequence having at least 95% sequence identity with SEQ ID NO: 3 is encoded by a polynucleotide having at least 70%, at least 80%, at least 85%, at least 90%, at least 93%, at least 95%, at least 96%, at least 97%, at least 98% and at least 99% sequence identity to the sequence of SEQ ID NO: 1. In a particularly preferred embodiment, the nucleic acid sequence encoding the asM of SEQ ID NO: 3 (AsaA) is the nucleic acid sequence of SEQ ID NO: 1.

As understood by those in the art, the quantity of asAA having GSH activity used in the compositions and methods of the present invention will depend on the enzymatic activity of the asM.

In general, asAA having GSH activity will be mixed with a slurry of a granular starch substrate in an amount of about 0.01 to 15.0 SSU per gram of dry solids content of the slurry. In some embodiments, the asAA having GSH activity is added in an amount of about 0.01 to 10.0 SSU, about 0.01 to 5.0 SSU; about 0.05 to 10.0 SSU; about 0.05 to 5.0 SSU; about 0.1 to 10.0 SSU; about 0.1 to 5.0 SSU; about 0.1 to 2.0 SSU; about 0.25 to 2.5 SSU; about 0.5 to 5.0 SSU; about 0.5 to 2.5 SSU; and also about 0.5 to 1.5 SSU per gram of dry solids content of the slurry.

Glucoamylases

Glucoamylases (GA) may be derived from bacteria, plants and fungi sources. Preferred glucoamylases useful in the compositions and methods of the invention are produced by several strains of filamentous fungi and yeast. In particular, glucoamylases secreted from strains of *Aspergillus* and *Trichoderma* are commercially important. Sources of these glucoamylases include: *Aspergillus niger* G1 and G2 glucoamylase and variants thereof (Boel et al., (1984) *EMBO J.* 3:1097–1102; WO 92/00381 and WO 00/04136); *Aspergillus awamori* glucoamylases (WO 84/02921); *Aspergillus oryzae* glucoamylase and variants thereof (Hata et al., (1991) *Agric. Biol. Chem.* 55:941–949) and *Aspergillus shirousami*. (See Chen et al., (1996) *Prot. Eng.* 9:499–505; Chen et al. (1995) *Prot Eng.* 8:575–582; and Chen et al., (1994) *Biochem J.* 302:275–281). Glucoamylases are also obtained from strains of *Talaromyces* such as those derived from *T. emersonii*, *T. leycettanus*, *T. duponti* and *T. thermophilus* (WO 99/28488; USP No. RE: 32,153; U.S. Pat. No. 4,587,215); strains of *Rhizopus*, such as *R. niveus* and *R. oryzae*; strains of *Mucor* and *Humicola*, such as *H. grisea* (See, Boel et al., (1984) *EMBO J.* 3:1097–1102; WO 92/00381; WO 00/04136; Chen et al., (1996) *Prot Eng.* 9:499–505; Taylor et al., (1978) *Carbohydrate Res.* 61:301–308; U.S. Pat. No. 4,514,496; U.S. Pat. No. 4,092,434; and Jensen et al., (1988) *Can. J. Microbiol.* 34:218–223).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) J. Biochem. 98:663–671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Gluc1 finds particular use in the present invention.

As understood by those in the art, the quantity of glucoamylase used in the method and compositions of the present invention depends on the enzymatic activity of the glucoamylase. Generally, an amount of between 0.001 and 10.0 GAU of glucoamylase per gram (ds) slurry adjusted to 20–45% dry solids may be added. In some embodiments, the glucoamylase is added in an amount between 0.01 and 10 GAU; between 0.01 and 5.0 GAU; between 0.05 and 5.0 GAU: between 0.1 and 10.0 GAU; between 0.1 and 5.0 GAU; between 0.1 and 2.0 GAU; between 0.25 and 1.5 GAU of glucoamylase per gram (ds) slurry. In one preferred embodiment, the dosage range for glucoamylase will be from 0.1 to 2.0 GAU/g (ds) slurry.

A particular group of glucoamylase (GA) enzymes are known as granular starch hydrolyzing enzyme(s) GSHE (See e.g., Tosi et al., (1993) *Can. J. Microbiol.* 39:846–855). GA-GSHEs not only have glucoamylase activity, but also are able to hydrolyze granular (raw) starch. GA-GSHEs have been recovered from fungal cells such as *Humicola* sp., *Aspergillus* sp. and *Rhizopus* sp. A *Rhizopus* oryzae GA-GSHE has been described in Ashikari et al., (1986) *Agric. Biol. Chem.* 50:957–964 and U.S. Pat. No. 4,863,864. Also reference is made to *Rhizopus niveus*. A *Humicola grisea* GA-GSHE is described by Allison et al., (1992) *Curr. Genet.* 21:225–229 and European Patent No., 171218. The gene encoding this enzyme is also known in the art as "gla1". An *Aspergillus awamori* var. *kawachi* GA-GSHE is described by Hayashida et al., (1989) *Agric. Biol. Chem* 53:923–929. An *Aspergillus shirousami* GA-GSHE is described by Shibuya et al., (1990) *Agric. Biol. Chem.* 54:1905–1914. One particular GA-GSHE preparation for use in the present invention includes enzyme preparations sold under the designation "M1" available from Biocon India, Ltd, India. The activity of a GA-GSHE preparation may be defined in terms of the glucoamylase activity.

In one embodiment, a GA-GSHE enzyme may be derived from a strain of *Humicola grisea*, particularly a strain of *H. grisea* var. *thermoidea* (See, U.S. Pat. No. 4,618,579). In some preferred embodiments, the *Humicola grisea* GA-GSHE enzyme is recovered from fungi including ATCC 16453, NRRL (USDA Northern Regional Research Laboratory, Peoria, Ill.) 15219, NRRL 15220, NRRL 15221, NRRL 15222, NRRL 15223, NRRL 15224 and NRRL 15225, as well as genetically altered strains thereof. These species produce enzymatic glucoamylase preparations that are immunologically the same (See, EP 0 171 218).

Recombinantly Expressed Enzymes

In some embodiments of the invention, microorganisms are genetically engineered to express heterologous asM having GSH activity and microorganisms may also be engineered to express heterologous glucoamylases. Preferred host cells are filamentous fungal cells. In a preferred embodiment, the filamentous fungal host is a strain of an *Aspergillus* sp, a *Trichoderma* sp, a *Fusarium* sp and a *Penicillium* sp. Particularly preferred fungal host cells include *A. nidulans, A. awamori, A. oryzae, A. aculeatus, A. niger, A. japonicus, T. reesei, T. viride, F. oxysporum*, and *F. solani*. *Aspergillus* strains are disclosed in Ward et al. (1993) *Appl. Microbiol. Biotechnol.* 39:738–743 and Goedegebuur et al., (2002) *Curr Gene* 41:89–98. In a most preferred embodiment, the host is a strain of *Trichoderma*, and particularly a strain of *T reesei*. Strains of *T. reesei* are known and nonlimiting examples include ATCC No. 13631, ATCC No. 26921, ATCC No. 56764, ATCC No. 56765, ATCC No. 56767 and NRRL 15709. In some preferred embodiments, the host strain is a derivative of RL-P37. RL-P37 is disclosed in Sheir-Neiss et al. (1984) *Appl. Microbiol. Biotechnology* 20:46–53.

In some preferred embodiments, a *Trichoderma* host cell or an *Aspergillus* host cell is genetically engineered to express an asAA having GSH activity characterized by an amino acid sequence having at least 90%, 95%, 96%, 97%, 98% and 99% identity with SEQ ID NO: 3. In some embodiments, the polynucleotide encoding an asM will have a nucleic acid sequence of SEQ ID NO: 1 or a nucleic acid sequence having at least 70% sequence identity with SEQ ID NO: 1.

In some embodiments, the asM produced in a host cell engineered to include a heterologous polynucleotide encoding an asM having GSH activity will have different, such as improved properties compared to the asM produced by the endogenous expression of the asAA having GSH activity in a native host. These properties may include for example, increased enzyme activity, increased enzyme stability at lower pH levels or increased specific activity.

In other embodiments, the host strain which is genetically engineered to express an asM having GSH activity may also be genetically engineered to express a heterologous GA.

The host strain may have been previously manipulated through genetic engineering. In some embodiments, various native genes of the fungal host cell will have been inactivated. These genes include, for example genes encoding cellulolytic enzymes, such as endoglucanases (EG) and exocellobiohydrolases (CBH) (e.g. cbh1, cbh2, egl1, egl2 and egl3). U.S. Pat. No. 5,650,322 discloses derivative strains of RL-P37 having deletions in the cbh1 gene and the cbh2 gene.

Vectors

While the description below refers specifically to asAA, one skilled in the art will readily understand that the same or similar methods apply to DNA constructs and vectors useful for introduction of a polynucleotide encoding GA into a host cell.

According to the invention, a DNA construct comprising nucleic acid encoding an asAA encompassed by the invention is constructed to transfer an asAA into a host cell. In one embodiment, the DNA construct is transferred to a host cell by an expression vector which comprises regulatory sequences operably linked to an asM coding sequence.

The vector may be any vector which when introduced into a fungal host cell is integrated into the host cell genome and is replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press pp. 396–428 and U.S. Pat. No. 5,874,276. Particularly useful vectors include pFB6, pBR322, PUC18, pUC100 and pENTR/D.

In preferred embodiments, nucleic acid encoding an asAA encompassed by the invention is operably linked to a suitable promoter, which shows transcriptional activity in the fungal host cell. The promoter may be derived from genes encoding proteins either homologous or heterologous to the host cell. Preferably, the promoter is useful in a *Trichoderma* host. Suitable nonlimiting examples of promoters include cbh1, cbh2, egl1, egl2. In one embodiment, the promoter is one that is native to the host cell. For example, when *T. reesei* is the host, the promoter is a native *T. reesei* promoter. In a preferred embodiment, the promoter is *T. reesei* cbh1, which is an inducible promoter and has been deposited in GenBank under Accession No. D86235. An "inducible promoter" is a promoter that is active under environmental or developmental regulation. In another embodiment, the promoter is one that is heterologous to the fungal host cell. Other examples of useful promoters include promoters from *A. awamori* and *A. niger* glucoamylase genes (Nunberg et al., (1984) *Mol. Cell Biol.* 4:2306–2315 and Boel et al., (1984) *EMBO J.* 3:1581–1585). Also, the promoters of the *T. reesei* xln1 gene and the cellobiohydrolase 1 gene may be useful (EPA 137280A1).

In some preferred embodiments, the asM coding sequence is operably linked to a signal sequence. The DNA encoding the signal sequence is preferably that which is naturally associated with the asAA gene to be expressed. Preferably, the signal sequence is encoded by an *Aspergillus kawachi* asaA gene that encodes an Ak-asaA. More preferably the signal sequence has at least 90%, at least 95%, at least 97%, and at least 99% sequence identity to the signal sequence of SEQ ID NO: 2. In additional embodiments, a signal sequence and a promoter sequence comprising a DNA construct or vector to be introduced into a fungal host cell are derived from the same source. For example, in some embodiments, the signal sequence is the cdh1 signal sequence which is operably linked to a cdh1 promoter.

In some embodiments, the expression vector also includes a termination sequence. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (Nunberg et al. (1984) supra, and Boel et al., (1984) supra).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS argB and pyr4. Markers useful in vector systems for transformation of *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6; and Kinghorn et al. (1992) APPLIED MOLECULAR GENETICS OF FILAMENTOUS FUNGI, Blackie Academic and Professional, Chapman and Hall, London). In a preferred embodiment, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475–479 and Penttila et al., (1987) *Gene* 61:155–164.

An expression vector comprising a DNA construct with a polynucleotide encoding an asM may be any vector which is capable of replicating autonomously in a given fungal host organism or of integrating into the DNA of the host. In some embodiments, the expression vector is a plasmid. In preferred embodiments, two types of expression vectors for obtaining expression of genes are contemplated.

The first expression vector comprises DNA sequences in which the promoter, asAA coding region, and terminator all originate from the gene to be expressed. In some embodiments, gene truncation is obtained by deleting undesired DNA sequences (e.g., DNA encoding unwanted domains) to leave the domain to be expressed under control of its own transcriptional and translational regulatory sequences.

The second type of expression vector is preassembled and contains sequences required for high-level transcription and a selectable marker. In some embodiments, the coding region for an asM gene or part thereof is inserted into this general-purpose expression vector such that it is under the transcriptional control of the expression construct promoter and terminator sequences. In some embodiments, genes or part thereof are inserted downstream of the strong cbh1 promoter.

Methods used to ligate the DNA construct comprising a polynucleotide encoding an asAA, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70–76.). Additionally, vectors can be constructed using known recombination techniques (e.g., Invitrogen Life Technologies, Gateway Technology).

Where it is desired to obtain a fungal host cell having one or more inactivated genes known methods may be used (e.g. methods disclosed in U.S. Pat. No. 5,246,853, U.S. Pat. No. 5,475,101 and WO92/06209). Gene inactivation may be accomplished by complete or partial deletion, by insertional inactivation or by any other means which renders a gene nonfunctional for its intended purpose (such that the gene is prevented from expression of a functional protein). Any gene from a *Trichoderma* sp or other filamentous fungal host, which has been cloned can be deleted, for example cbh1, cbh2, egl1 and eg/2 genes. In some embodiments, gene deletion may be accomplished by inserting a form of the desired gene to be inactivated into a plasmid by methods known in the art. The deletion plasmid is then cut at an appropriate restriction enzyme site(s), internal to the desired gene coding region, and the gene coding sequence or part thereof is replaced with a selectable marker. Flanking DNA sequences from the locus of the gene to be deleted (preferably between about 0.5 to 2.0 kb) remain on either side of the marker gene. An appropriate deletion plasmid will generally have unique restriction enzyme sites present therein to enable the fragment containing the deleted gene, including the flanking DNA sequences and the selectable markers gene to be removed as a single linear piece.

Transformation, Expression and Culture of Host Cells

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53–56). The expression of heterologous protein in *Trichoderma* is described in U.S. Pat. No. 6,022,725; U.S. Pat. No. 6,268,328; Harkki et al. (1991); *Enzyme Microb. Technol.* 13:227–233; Harkki et al., (1989) *Bio Technol.* 7:596–603; EP 244,234; EP 215,594; and Nevalainen et al., "The Molecular Biology of *Trichoderma* and its Application to the Expression of Both Homologous and Heterologous Genes", in MOLECULAR INDUSTRIAL MYCOLOGY, Eds. Leong and Berka, Marcel Dekker Inc., NY (1992) pp. 129–148). Reference is also made to Cao et al., (2000) *Sci.* 9:991–1001 for transformation of *Aspergillus* strains.

Preferably, genetically stable transformants are constructed with vector systems whereby the nucleic acid encoding an asAA is stably integrated into a host strain chromosome. Transformants are then purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

In one specific embodiment, the preparation of *Trichoderma* sp. for transformation involves the preparation of protoplasts from fungal mycelia. (See, Campbell et al., (1989) *Curr. Genet.* 16:53–56). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. Besides the need for the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL, preferably $2 \times 10^6$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. (See, e.g., U.S. Pat. Nos. 6,022,725 and 6,268,328, both of which are incorporated by reference).

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only.

Generally, cells are cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71–86, 1988 and Ilmen, M. et al., (1997) *Appl. Environ. Microbiol.* 63:1298–1306). Common commercially prepared media (e.g., Yeast Malt Extract (YM) broth, Luria Bertani (LB) broth and Sabouraud Dextrose (SD) broth) also find use in the present invention.

Culture conditions are also standard, (e.g., cultures are incubated at approximately 28° C. in appropriate medium in shake cultures or fermenters until desired levels of asAA expression are achieved). Preferred culture conditions for a given filamentous fungus are known in the art and may be found in the scientific literature and/or from the source of the fungi such as the American Type Culture Collection and Fungal Genetics Stock Center.

After fungal growth has been established, the cells are exposed to conditions effective to cause or permit the expression of an asAA as defined herein. In cases where an asM having GSH activity coding sequence is under the control of an inducible promoter, the inducing agent (e.g., a sugar, metal salt or antimicrobial), is added to the medium at a concentration effective to induce asM expression.

Identification of asAA Activity

In order to evaluate the expression of an asAA having GSH activity by a cell line that has been transformed with a heterologous polynucleotide encoding an asaA encompassed by the invention, assays can be carried out at the protein level, the RNA level or by use of functional bioassays particular to alpha amylase activity and/or production. In general assays employed include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of an asAA having GSH activity may be measured in a sample directly, for example, by assays directly measuring reducing sugars such as glucose in the culture media and by assays for measuring glucoamylase activity, expression and/or production. Substrates useful for assaying GSH activity include granular starch substrates. For example, glucose concentration may be determined by any convenient method such as by using glucose reagent kit No 15-UV (Sigma Chemical Co.) or an instrument such as Technicon Autoanalyzer. Also reference is made to glucose oxidase kits and glucose hexose kits commercially available from Instrumentation Lab. (Lexington, Mass.).

In addition, gene expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of an asaA. The details of such methods are known to those of skill in the art and many reagents for practicing such methods are commercially available.

In addition, gene expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a asAA. The details of such methods are known to those of skill in the art and many reagents for practicing such methods are commercially available.

Alpha amylase activity may be measured by using the DNS method as described in Miller, G. L. (1959) Anal. Chem. 31:426–428. Glucoamylase activity may be assayed by the 3,5-dinitrosalicylic acid (DNS) method (See, Goto et al., (1994) Biosci. Biotechnol. Biochem. 58:49–54).

In some embodiments of the invention, the asAA having GSH activity expressed by a *Trichoderma* or *Aspergillus* host will be greater than 1 gram protein per liter (g/L), greater than 2 g/L, greater than 5 g/L, greater than 10 g/L, greater than 20 g/L, greater than 25 g/L, greater than 30 g/L, greater than 50 g/L and also greater than 100 g/L of culture media.

Methods for Purifying asAA

In general, an asaA (including n-asAA or r-asAA) produced in cell culture is secreted into the medium and may be purified or isolated, e.g., by removing unwanted components from the cell culture medium. In some cases, an AsaA may be produced in a cellular form necessitating recovery from a cell lysate. In such cases the enzyme is purified from the cells in which it was produced using techniques routinely employed by those of skill in the art. Examples include, but are not limited to, affinity chromatography (Tilbeurgh et al., (1984) *FEBS Lett.* 16:215); ion-exchange chromatographic methods (Goyal et al., (1991) *Biores. Technol.* 36:37; Fliess et al., (1983) *Eur. J. Appl. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (Medve et al., (1998) *J. Chromatography A* 808:153; hydrophobic interaction chromatography (Tomaz and Queiroz, (1999) *J. Chromatography A* 865:123; two-phase partitioning (Brumbauer, et al., (1999) *Bioseparation* 7:287); ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75.

Fermentations

In some embodiments of the present invention, fungal cells expressing a heterologous glucoamylase and/or asAA are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Compositions and Methods

In one embodiment, a granular starch substrate is contacted with an asAA having GSH activity, wherein the asAA is available as a cell free filtrate (for example wherein the asAA is isolated from a culture medium). In another embodiment, the granular starch substrate is contacted with an asAA having GSH activity, wherein the asAA is available in a culture medium containing the fungal host cells which express and secret the asAA having GSH activity.

In other embodiments, the granular starch substrate is contacted in the same step with both an asAA having GSH activity and a glucoamylase (GA) to hydrolyze the granular starch. The GA may also be available as a cell free filtrate or in the culture medium containing host cells that express and secrete the GA.

A particularly useful granular starch hydrolyzing enzyme composition, according to the invention includes a mixture of GA (e.g., DISTALLASE®) and an asAA having at least 90% or at least 95% sequence identity to SEQ ID NO: 3. In some embodiments, the range of asAA present in this mixture measured as activity is from 0.01 to 15.0 SSU, and the amount of glucoamylase useful in this combination is in the range of 0.1 to 10.0 GAU/g ds.

A particularly useful enzymatic composition includes a mixture of an asAA having at least 95% sequence identity to SEQ ID NO: 3 and a GA having 0.1 to 10 GAU/g ds. Another particularly useful enzymatic composition includes a mixture of an asAA having at least 98% sequence identity to SEQ ID NO: 3 and a GA having 0.1 to 10 GAU/g ds.

In some embodiments, the ratio of asAA having GSH activity (SSU) to GA activity (GAU) will be in the range of 15:1 to 1:15. In further embodiments, the ratio (SSU to GAU) will be in the range of about 10:1 to 1:10; about 10:1 to 1:5; about 5:1 to 1:5; about 4:1 to 1:4; about 3:1 to 1:3;

about 2:1 to 1:4 and also about 2:1 to 1:2. In some preferred embodiments, the ratio of SSU to GAU will be between about 4:1 to 2:1.

In one embodiment, an enzyme composition comprising either an asaA alone or in combination with a glucoamylase will be added to a slurry of a granular starch substrate and the mixture will be fermented in a single step. The slurry may have about 10–50% ds; about 10–45%; about 15–40%; about 20–40%; about 25–40%; or about 25–35% ds.

The exact amounts of the components encompassed by the composition and methods of the invention depend on the combination of enzymes applied as well as the type of granular starch processed.

In some embodiments the invention relates to a method of producing an end-product comprising contacting a slurry of a granular starch substrate with a combination of enzymes including glucoamylase and an acid stable alpha amylase (asAA) having granular starch (GSH) activity in one-step to produce the end-product. In some embodiments, the asAA and GA will be added separately and in other embodiments, the asAA and GA will be added in a combination blend. In a preferred embodiment, the contacting step is conducted at a temperature below the starch gelatinization temperature of the granular starch.

The exact temperature used in accordance with the methods of the invention depends upon the specific starch substrate used. General starch gelatinization temperature ranges are disclosed in Swinkels pages 32–38 in STARCH CONVERSION TECHNOLOGY, eds Van Beynum et al., (1985) Marcel Dekker Inc., NY and THE ALCOHOL TEXTBOOK, A REFERENCE FOR THE BEVERAGE, FUEL AND INDUSTRIAL ALCOHOL INDUSTRIES, 3$^{rd}$ Ed., eds Jacques et al., 1999, Nottingham University Press, UK. In some embodiments the temperature will be least about 10° C., 15° C., 20° C., 25° C., 30° C., 35° C., 40° C., 45° C., 50° C., 55° C., 60° C., and 65° C. In other embodiments, the temperature will be between about 30–65° C., about 35–65° C., about 40–65° C., and about 45–65° C. In other embodiments, the temperature will be between about 25–45° C., about 25–40° C. and about 30–35° C. In preferred embodiments, the starch substrate is never subjected to the thermal conditions used for liquefactions.

In some embodiments, the residence time of the method is from about 2 to 300 hrs, but more typically from 2 to 120 hours. In some embodiments, the process is conducted from about 5 to 100 hours. In other embodiments, the process is conducted from about 5 to 80 hours. In still other embodiments, the process is conducted for at least 5 hours but less than 100 hours. In other embodiments, the process is conducted for at least about 10 hours but less than about 100 hours.

In some embodiments, at least 60%, 65%, 70%, 75%, 80%, 85%, 90%, 94%, 95%, 96%, 97%, 98% and 99% of the dry solids of the granular starch is hydrolyzed. In some embodiments, the granular starch substrate is completely hydrolyzed. In some embodiments, at least 90% of the granular starch is hydrolyzed in 100 hours. In certain embodiments, at least 90% of the granular starch substrate is hydrolyzed in a time period of 24 hours. In other embodiments, at least 95% of the granular starch substrate is hydrolyzed in a time period of 24 hours.

The yield of glucose (percent of the total solubilized dry solids) may be at least about 85%, 90%, 91%, 92%, 93%, 94%, 95%, 96%, 97% and 98%. However, in a preferred embodiment, the glucose is continually produced and substantially all of the glucose is used in the process to produce an end-product, such as ethanol. (Reference is made to MOLECULAR STRUCTURE AND FUNCTION OF FOOD CARBOHYDRATE, ED. G.G. BIRCH ET AL, APPLIED SCIENCE PUBLISHERS, LONDON).

Additional enzymes may be included in the compositions and methods encompassed by the invention. These additional enzymes, which find use in the present invention include debranching enzymes such as pullulanases (E.C. 3.2.1.41) and isoamylases (E.C. 3.2.1.68). Such enzymes hydrolyze alpha-1,6-glucosidic bonds. Thus, during the hydrolysis of the starch, debranching enzymes remove successive glucose units from the non-reducing ends of the starch.

Another enzyme that may be used in the compositions of the invention are beta-amylases (E.C. 3.2.1.2). These are exo-acting maltogenic amylases, which catalyze the hydrolysis of 1,4-alpha-glucosidic linkages in amylose, amylopectin and related glucose polymers. The enzymes are characterized as having an optimum pH range from 4.5 to 7.0 and optimum temperature range from 40° C. to 65° C. Commercial beta-amylases are available from Genencor International Inc.

Further additional enzymes which may be used are proteases, such as fungal and bacterial proteases. Fungal proteases include for example, those obtained from *Aspergillus, Mucor* and *Rhizopus,* such as *A. niger, A. awamori, A. oryzae* and *M. miehei*. Other enzymes include but are not limited to cellulases, hemicellulases, lipases and cutinases.

The effective amount of these enzymes to be included in the methods of the invention can be readily determined by one skilled in the art.

In some embodiments, an antimicrobial may be added to the compositions and fermentation medium of the invention. Antimicrobials are compounds that kill or inhibit the growth of microorganisms.

In another embodiment, the granular starch substrate may be pretreated prior to contacting with the asAA and optionally the GA. Pretreatment includes heating a granular starch substrate, preferably a slurry containing the raw substrate to a temperature below the starch gelatinization temperature of the starch substrate prior to the fermentation or culturing with an enthanologenic microorganism. In preferred embodiments, the pretreatment will include the use of an alpha amylase, such as a bacterial alpha amylase (i.e., SPEZYME and GZYME 997 (Genencor International, Inc.)).

In some embodiments, the pretreatment will be included in the culture with an asAA having GSH activity according to the invention and optionally with a glucoamylase. In other embodiments, the pretreatment will be separate from the culture which includes the asAA having GSH activity and optionally the glucoamylase. In some embodiments the pretreatment will take place from about 2–24 hours. In other embodiments, the pretreatment will take place from about 2 to 8 hours.

In some preferred embodiments, the method comprises a simultaneous saccharification and fermentation (SSF), wherein the granular starch hydrolysis step and a fermentation step are carried out contemporaneously. The culture medium, which includes the granular starch substrate contacted with asAA having GSH activity, either supplied in a cell free filtrate or expressed from a fungal host cell in the culture, will also include microorganisms, such as bacteria, fungal or yeast and particularly ethanolgenic microorganisms. In some embodiments, the fermentation system may include at least two cell cultures. In some preferred embodiments, the SSF will include contacting the granular starch substrate with a glucoamylase in addition to the asAA having GSH activity.

In some preferred embodiments the ethanologenic microorganisms will include yeast, such as *Saccharomyces cerevisiae* (U.S. Pat. No. 4,316,956). Preferred examples of ethanologenic microorganisms also include bacteria expressing alcohol dehydrogenase and pyruvate decarboxylase such as can be obtained with or from *Zymomonas moblis* (U.S. Pat. Nos. 5,028,539; 5,424,202; 5,487,989; 5,482,846; 5,554,520; and 5,514,583). In additional embodiments, the ethanologenic microorganisms express xylose reductase and xylitol dehydrogenase, enzymes that convert xylose to xylulose. Commercial sources of yeast include FALI; RED STAR (Red Star); FERMIOL (DSM Specialties) and SUPERSTART (Alltech).

In some embodiments, the residence time for the simultaneous saccharification and fermentation will be from about 2 to 300 hours, but preferably from 2 to 120 hours. In some embodiments, the time is from about 5 to 100 hours. In other embodiments, the time is from about 5 to 80 hours. In still other embodiments, the time is for at least 5 hours but less than 100 hours. In other embodiments, the process time is for at least about 10 hours but less 100 hours at a temperature between 10–40° C. and preferably between 25–40° C. and a pH of 3.5 to 6.0. The use of yeast in fermentation is well known and reference is made to THE ALCOHOL TEXTBOOK, K. JACQUES ET AL., EDS. 1999, NOTTINGHAM UNIVERSITY PRESS, UK.

In some embodiments at least 5 vol %, at least 8 vol %, at least 10 vol %, at least 12 vol %, at least 15 vol % and at least 18 vol % of ethanol will be produced in the fermentation media. In other embodiments, the amount of ethanol produced in the fermentation media will be between 5–30%, also between 5–25%, and between 5–20%.

Following the fermentation, alcohol (i.e., ethanol) may be recovered from the fermentation media by means known in the art. In some embodiments, the alcohol in the fermented medium may be distilled, for example by heating or vacuum distillation. The ethanol may then be used, for example, as fuel ethanol or potable ethanol. The remaining residue, known as stillage may also be recovered and components of the stillage recycled for the next fermentation or the stillage may be separated into a soluble fraction or insoluble fraction.

When the stillage is separated for example by centrifugation or screening into a soluble fraction and an insoluble fraction, these fractions can be used to make distillers' solubles or distillers' dried solubles or mixed together to make distillers' dried grain plus solubles (DDGS). One skilled in the art is familiar with processes for forming DDGS and distillers' grains in general. In some embodiments of the invention, when % ethanol increases in the fermentation process, the amount of DDGS decreases. However, one significant advantage of the method encompassed by the invention may be an increase in the % total protein in the DDGS and reference is made to example 10. The DDGS may then be used for example, in an animal feed formulation.

In some embodiments, the SSF process encompassed by the invention will result in a DDGS containing less than 30%, less than 15%, less than 10%, less than 9%, less than 8%, less than 7%, less than 6%, less than 5%, less than 4%, less than 2% and less than 1% residual starch. It is contemplated that the DDGS which results from the process according to the invention while having lower residual starch content compared to DDGS prepared by prior art processes will actually have an increased total amount of protein and therefore be of additional benefit for used in animal feeds.

Figure 12:
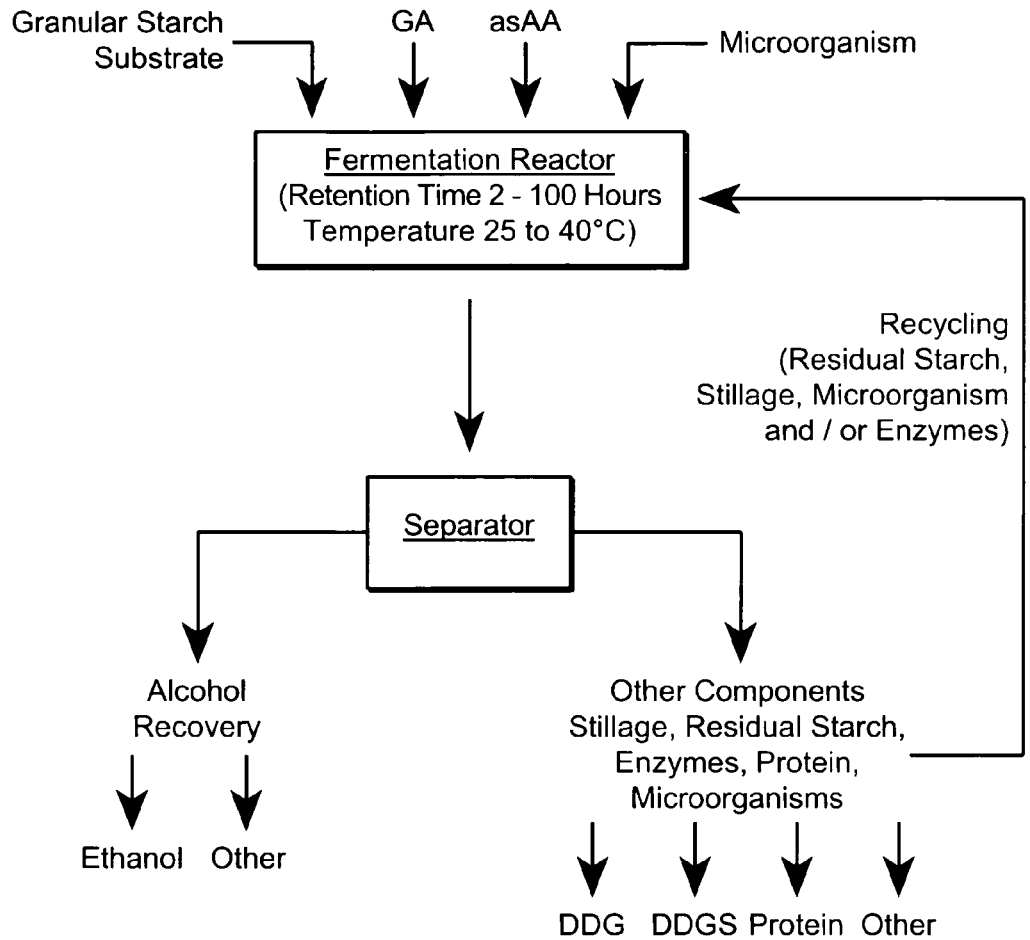
FIG. 12 is a schematic diagram, which illustrates an embodiment of the invention. This embodiment comprises combining a granular starch substrate with glucoamylase, asAA and microorganisms in a reactor to allow fermentation in a single step under conditions that include fermentation for 2 to 100 hours at a temperature of 25–40° C. The mixture that is produced in the fermentation is separated. Alcohol may be recovered from the separation, and ethanol may be produced. In addition, a mixture of non-fermented solids and water may be recovered. The mixture of non-fermented solids and water, which includes residual starch, stillage, proteins, and microorganisms, may be further processed to yield products such as DDG and DDGS or the components of the mixture (individually or combined) may be recycled back to the reactor for further fermentation.

The residual starch which is recovered from the fermentation may be recycled along with enzymes and/or microorganisms and subjected to renewed fermentation. In one embodiment, means for fermenting a granular starch slurry of 20–50% ds contemporaneously with an asaA and glucoamylase and microorganism will result in residual starch when fermentation has proceeded to the intended alcohol content (e.g., 8 to 30%). The residual starch, the microorganisms and/or the residual enzymes may be mixed with fresh granular starch and additional aliquots of enzyme as needed to produce a fermentation charge for another fermentation. However, it is not intended that the invention be limited to recycling the enzymes and/or microorganisms with the residual starch. In some embodiments, the microorganisms are removed from the residual starch prior to recycling of the residual starch and in other embodiments, only the microorganisms are recycled. An example of the various embodiments presented herein is observed in FIG. 12.

While in preferred embodiments, the desired end-product is ethanol, the desired end-product may be any product that may be produced by the enzymatic conversion of the granular starch substrate. Glucose obtained from the hydrolysis of granular starch may be bioconverted into numerous products such as but not limited to ascorbic acid intermediates (e.g., gluconate, 2-keto-L-gulonic acid, idonate, 5-keto-gluconate and 2,5-diketogluconate); 1,3-propanediol; aromatic amino acids (e.g. tyrosine, phenylalanine and tryptophan); organic acids (e.g. lactate, succinate, isocitrate and oxaloacetate); amino acids (serine and glycine); pyruvate and others. One skilled in the art is aware of various fermentation conditions which may be used in the production of these end-products and enzyme assays to measure the levels of protein expression.

Experimental

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply:

asAA having GSH activity (an acid-stable alpha amylase having granular starch hydrolyzing activity); asaA (an acid-stable alpha amylase having granular starch hydrolyzing activity as illustrated in SEQ ID NO: 3 and which has been obtained from the endogenous expression of an asAA in *Aspergillus kawachi*); Tr-asaA (the expression of the *A. kawachi* acid-stable alpha amylase expressed in a *Trichoderma reesei* host); AkAA (the acid stable alpha amylase having SEQ ID NO: 3 and sometimes used interchangeability with asaA); and other abbreviations including GA (glucoamylase); wt % (weight percent); ° C. (degrees Centigrade); rpm (revolutions per minute); $H_2O$ (water); $dH_2O$ (deionized water); $dIH_2O$ (deionized water, Milli-Q filtration); aa (amino acid); bp (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); U (units); V (volts); MW (molecular weight); sec (seconds); min(s) (minute/minutes); hr(s) (hour/hours); PAGE (polyacrylamide gel electrophoresis);

DO (dissolved oxygen); phthalate buffer (sodium phthalate in water, 20 mM, pH 5.0); PBS (phosphate buffered saline [150 mM NaCl, 10 mM sodium phosphate buffer, pH 7.2]); SDS (sodium dodecyl sulfate); Tris (tris(hydroxymethyl) aminomethane); w/v (weight to volume); w/w (weight to weight); v/v (volume to volume); Genencor (Genencor International, Inc., Palo Alto, Calif.); DDGS (Distilleries Dry Grain plus Solids); MT (Metric ton); and EtOH (ethanol).

The following assays and methods are used in the examples provided below:

Glucoamylase assay: Glucoamylase activity was measured using a well-known assay which is based on the ability of glucoamylase to catalyze the hydrolysis of p-nitrophenyl-alpha-D-glucopyranoside (PNPG) to glucose and p-nitrophenol. At an alkaline pH, the nitrophenol; forms a yellow color that is proportional to glucoamylase activity and is monitored at 400 nm and compared against an enzyme standard measured as a GAU.

One "Glucoamylase Activity Unit" (GAU) is defined as the amount of enzyme that will produce 1 µm of reducing sugar, calculated as glucose per hour from a soluble starch substrate (4% ds) at pH 4.2 and 60° C.

The measurement of acid-stable alpha amylase activity is based on the degree of hydrolysis of soluble potato starch substrate (4% ds) by an aliquot of the enzyme sample at pH 4.5, 50° C. The reducing sugar content is measured using the DNS method as described in Miller, G. L. (1959) *Anal. Chem.* 31:426–428. One unit of the enzyme activity (SSU, soluble starch unit) is equivalent to the reducing power of 1 mg of glucose released per minute at the specific incubation conditions.

Determination of total starch content: The enzyme-enzyme starch liquefaction and saccharification process was used to determine the total starch content. In a typical analysis, 2 g of the dry sample was taken in a 100 ml Kohlraucsh flask and 45 ml of MOPS buffer, pH 7.0 was added. The slurry was well stirred for 30 min. SPEZYME FRED (1:50 diluted in water), 1.0 ml was added and heated to boiling for 3–5 min. The flask was placed in an autoclave maintained at 121° C. for 15 min. After autoclaving the flask was placed in a water bath at 95° C. and 1 ml of 1:50 dilutes SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX L-400 (Glucoamylase from Genencor International Inc.) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

Residual starch iodine test: A sample of the beer (fermentation broth) was centrifuged in 2 ml plastic centrifuge tubes. The supernatant was decanted and the tube containing the pellet was placed in an ice bath. Several drops of 0.025N iodine solution (0.1 N iodine from VWR Cat. No. VW3207-1 diluted 4×) was added to the pellet and mixed. A positive (+) starch shows a range of color from blue to purple and the intensity of color is directly proportional to the concentration of starch. A negative result (−) remains yellowish.

Total protein analysis: The total nitrogen (N) in the sample preparations was determined using the Kjeldhal method (American Assoc. Cereal Chemists (MCC), (1983), Methods 22B60 8th Ed. St Paul, Minn.). Protein content was calculated by 6.25×total N.

Ethanol and Carbohydrate Determinations:

Ethanol and carbohydrate composition of the samples were determined using the HPLC method as described herein:

a) a 1.5 mL Eppendorf centrifuge tube was filled with fermentor beer and cooled on ice for 10 min;
b) the sample tube was centrifuged for 1 min in Eppendorf table top centrifuge;
c) a 0.5 mL sample of the supernatant was transferred to a test tube containing 0.05 mL of Kill solution (1.1N $H_2SO_4$) and allowed to stand for 5 min;
d) 5.0 mL of water is added to the test tube sample and then filtered into a HPLC vial through 0.45 µm Nylon Syringe Filter; and
e) run on HPLC.

HPLC Conditions:
a) Ethanol System:
    Column: Phenomenex Rezex Organic Acid Column (RHM-Monosaccharide) #00H-0132-KO (Equivalent to Bio-Rad 87H)
    Column Temperature: 60° C.
    Mobile Phase: 0.01 N $H_2SO_4$
    Flow Rate: 0.6 mL/min
    Detector: RI
    Injection Volume: 20 µL
b) Carbohydrate System:
    Column: Phenomenex Rezex Carbohydrate (RCM-Monosaccharide) #00H-0130-KO (Equivalent to Bio-Rad 87H)
    Column Temperature: 70° C.
    Mobile Phase: Nanopure DI $H_2O$
    FlowRate: 0.8 mL/min
    Detector: RI
    Injection Volume: 10 µL (3% DS material)

The column separates based on the molecular weight of the saccharides, which are designated as DP1 (monosaccharides); DP2 (disaccharides); DP3 (trisaccharides) and DP+4 (oligosaccharide sugars having a degree of polymerization greater than 3).

Preparation of asaA used in examples 7–12 was as follows. At the end of the fermentation of the *T. reesei* which expresses asaA (prepared according to examples 2 and 3), the biomass was separated by centrifugation and the clear culture filtrate was concentrated using a 10,000 molecular weight cut-off ultrafiltration membrane. This ultrafiltrated concentrate having (90 SSU/g) was used.

Preparation of glucoamylase used in examples 7–12 was as follows: A selected fungal strain of *Aspergillus niger* as described in U.S. Pat. No. 3,249,514 was used. After fermentation, fungal mycelia were separated using conventional separation methods including filtration centrifugation. The clear filtrate was concentrated by ultrafiltration at 5° C. to a specified activity.

EXAMPLE 1

Cloning the *Aspergillus kawachi* Acid-Stable Alpha-Amylase Gene

Genomic DNA was extracted from an overnight culture of *A. kawachi* mycelia. The FastDNA Kit (QbioGene, Carlsbad, Calif.) SPIN™ protocol was used according to the manufacturer's instructions for fungi. For homogenization, the sample was processed for 30 sec at speed 4.0 on a FastPrep Instrument. PCR primers were designed, based on the asaA sequence of A. Kaneko, et al. (Kaneko et al., (1996), *J. Ferm Bioeng* 81:292–298). The forward primer contained a motif for directional cloning into the pENTR/D vector (Invitrogen).

The sequence of the alpha6 primer was CACCAT-GAGAGTGTCGACTTCMG (SEQ ID NO. 6) and the sequence of the Akaa3 primer was CTACCTCCACGTATC-MCCAC (SEQ ID NO. 7).

The 2.36 kb PCR product was purified by gel extraction (Gel Purification kit, Qiagen) and cloned into pENTR/D, according to the Invitrogen Gateway system protocol. The vector was then transformed into chemically competent Top10 *E. coli* (Invitrogen) with kanamycin selection. Plasmid DNA from several clones was digested with restriction enzymes to confirm the correct size insert. The alpha-amylase gene insert was sequenced (Sequetech, Mountain View, Calif.) from several clones (SEQ ID NO: 1). Plasmid DNA from one clone, pENTR/D_Akaa#11, was added to the LR clonase reaction (Invitrogen Gateway system) with pTrex3g/amdS destination vector DNA. Recombination, in the LR clonase reaction, replaced the CmR and ccdB genes of the destination vector with the *A. kawachi* asaA from the pENTR/D vector. This recombination directionally inserted asaA between the cbh1 promoter and terminator of the destination vector. Recombination site sequences of 48 and 50 bp remained upstream and downstream, respectively, of the alpha amylase. An aliquot of the LR clonase reaction was transformed into chemically competent Top10 *E. coli* and grown overnight with carbenicillin selection. Plasmid DNA from several clones was restriction digested to confirm the correct insert size. Plasmid DNA from one clone, pTrex3g_Akalpha#1 (FIG. 4) was digested with EcoRI to release the expression cassette including the cbh1 promoter: asaA:cbh1 terminator:amdS. This 7.8 kb cassette was purified by agarose extraction using standard techniques and transformed into a strain of *T. reesei* derived from the publicly available strain QM6a, as further described below.

EXAMPLE 2

Biolistic Transformation of *T. reesei*.

A *Trichoderma reesei* spore suspension was spread onto the center ~6 cm diameter of an MABA transformation plate (150 µl of a 5×10$^7$–5×10$^8$ spore/ml suspension). The plate was then air dried in a biological hood. The stopping screens (BioRad 165–2336) and macrocarrier holders (BioRad 1652322) were soaked in 70% ethanol and air dried. DriRite desiccant was placed in small Petri dishes (6 cm Pyrex) and overlaid with Whatman filter paper. The macrocarrier holder containing the macrocarrier (BioRad 165–2335) was placed flatly on top of filter paper and the Petri dish lid replaced.

A tungsten particle suspension was prepared by adding 60 mg tungsten M-10 particles (microcarrier, 0.7 micron, Bio-Rad #1652266) to an Eppendorf tube. 1 ml ethanol (100%) was added. The tungsten was votexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 ml of sterile 50% glycerol. The tungsten was prepared fresh at least every two weeks.

The transformation reaction was prepared by adding 25 µl of suspended tungsten to a 1.5 ml Eppendorf tube for each transformation. Subsequent additions were made in order, 0.5–5 µl DNA (Xbal-digested expression cassette), 25 µl 2.5M $CaCl_2$, 10 µl 0.1 M spermidine. The reaction was vortexed continuously for 5–10 minutes, keeping the tungsten suspended. The Eppendorf tube was then microfuged briefly and decanted. The tungsten pellet was washed with 200 µl of 70% ethanol, microfuged briefly to pellet and decanted. The pellet was washed with 200 µl of 100% ethanol, microfuged briefly to pellet, and decanted. The tungsten pellet was resuspended in 24 µl 100% ethanol. The Eppendorf tube was placed in an ultrasonic water bath for 15 seconds and 8 µl aliquots were transferred onto the center of the desiccated macrocarriers. The macrocarriers were left to dry in the desiccated Petri dishes.

A He tank was turned on to 1500 psi. 1100 psi rupture discs (BioRad 165–2329) were used in the Model PDS-1000/He Biolistic Particle Delivery System (BioRad). When the tungsten solution was dry, a stopping screen and the macrocarrier holder were inserted into the PDS-1000. An MABA plate, containing the target *T. reesei* spores, was placed 6 cm below the stopping screen. A vacuum of 29 inches Hg was pulled on the chamber and held. The He Biolistic Particle Delivery System was fired. The chamber was vented and the MABA plate removed for incubation at 28° C. until colonies appeared (5 days).

With reference to this Example 2 the following solutions were prepared,

| Modified amdS Biolistic agar (MABA) | per liter |
|---|---|
| Part I, make in 500 ml dH$_2$O | |
| 1000x salts | 1 ml |
| Noble agar | 20 g |
| pH to 6.0, autoclave | |
| Part II, make in 500 ml dH$_2$O | |
| Acetamide | 0.6 g |
| CsCl | 1.68 g |
| Glucose | 20 g |
| KH$_2$PO$_4$ | 15 g |
| MgSO$_4$.7H$_2$O | 0.6 g |
| CaCl$_2$.2H$_2$O | 0.6 g |
| pH to 4.5, 0.2 micron filter sterilize; | |
| leave in 50° C. oven to warm, add to agar, | |
| mix, pour plates. Stored at room temperature. | |

| 1000x Salts | per liter |
|---|---|
| FeSO$_4$.7H$_2$O | 5 g |
| MnSO$_4$.H$_2$O | 1.6 g |
| ZnSO$_4$.7H$_2$O | 1.4 g |
| CoCl$_2$.6H$_2$O | 1 g |
| Bring up to 1 L dH$_2$O. | |
| 0.2 micron filter sterilize | |

EXAMPLE 3

PEG-Mediated Protoplast Fusion Transformation of *T. reesei*.

A 1–2 cm$^2$ agar plug of a sporulated mycelia (grown on potato dextrose agar (PDA), Difco for 5 days at 30° C.) was inoculated into 50 ml of YEG (5 g/L yeast extract plus 20 g/L glucose) broth in a 250 ml, 4-baffle shake flask and incubated at 30–37° C. for 16–20 hours at 200 rpm. The mycelia were recovered by transferring the shake flask contents into 50 ml conical tubes and spinning at 2500 rpm for 10 minutes. The supernatant was discarded and the mycelial pellet was transferred into a 250 ml, 0.22 m CA or PES Corning filter bottle containing 40 ml of filtered β-D- glucanase solution. The solution was incubated at 30° C., 200 rpm, for 2 hours to generate protoplasts. Protoplasts were harvested by filtration, through sterile Miracloth (Cal-Biochem, La Jolla, Calif.), into a 50 ml conical tube. The protoplasts were pelleted by centrifugation at 2000 rpm for 5 minutes and the supernatant discarded. Protoplast pellets were washed once with 50 ml of 1.2 M sorbitol; centrifuged (2000 rpm, 5 min.) and supernatant was discarded. The pellet was washed with 25 ml of sorbitol/$CaCl_2$. A haemocytometer was used to count the protoplasts and then pelleted by centrifugation at 2000 rpm for 5 min. The supernatant was discarded and protoplast pellets resuspended in a volume of sorbitol/$CaCl_2$ sufficient to generate a protoplast solution with a protoplast concentration of $1.25 \times 10^8$/ml.

For each transformation, an aliquot of 20 µg of expression vector DNA (in a is volume no greater than 20 µl) was transferred into 15 ml conical tubes, on ice. Protoplast suspension (200 µl) and 50 µl PEG solution was added to each tube. This was mixed gently and incubated on ice for 20 min. PEG (2 ml) solution was added to each transformation tube and incubated at room temperature for 5 minutes. 4 ml sorbitol/$CaCl_2$ solution was added to each tube (total volume 6.2 ml) and mixed gently. Then 2 ml of the transformation mixture was added to each of 3 molten (50° C.) top agar tubes. Each top agar mixture was poured onto a separate transformation plate and incubated at 30° C. for four to seven days.

For transformation with amdS selection, acetamide/sorbitol plates and top agar were used. Selection plates were the same as transformation plates, but without sorbitol. Putative transformants were purified by transferring isolated colonies to fresh selective media containing acetamide.

Media and solutions were prepared as follows.
1) 40 ml β-D-glucanase solution—dissolved 600 mg β-D-glucanase (InterSpex Products Inc., San Mateo, Calif.) and 400 mg $MgSO_4.7H_2O$ in 40 ml 1.2M sorbitol.
2) 200 ml PEG mix—Dissolved 50 g PEG 4000 (BDH Laboratory Supplies Poole, England) and 1.47 g $CaCl_2.2H_2O$ in 200 ml $dlH_2O$. Prepared fresh monthly.
3) Sorbitol/$CaCl_2$ solution—Dissolved 50 mM $CaCl_2$ in 1.2M sorbitol.
4) Acetamide/sorbitol agar—
   Part 1—Dissolved 0.6 g acetamide (Aldrich, 99% sublime.), 1.68 g CsCl, 20 g glucose, 20 g $KH_2PO_4$, 0.6 g $MgSO_4.7H_2O$, 0.6 g $CaCl_2.2H_2O$, 1 ml 1000× salts (see below) in 200 ml $dlH_2O$, adjusted to pH 5.5, brought volume up to 300 mls with $dH_2O$, and filter sterilized.
   Part II—20 g Noble agar and 218 g sorbitol were added to a 1 L cylinder, brought to volume (700 mls) with $dlH_2O$, and autoclaved.
   Part II was added to Part I for a final volume of 1 L.
5) 1000× Salts—Combined 5 g $FeSO_4.7H_2O$, 1.6 g $MnSO_4$—$H_2O$, 1.4 g $ZnSO_4.7H_2O$, 1 g $CoCl_2.6H_2O$ and brought the volume up to 1 L with $dlH_2O$. Filter sterilized.

EXAMPLE 4

PEG-Mediated Protoplast Fusion Transformation of *Aspergillus niger*

A 2 $cm^2$ agar plug was inoculated from a sporulated *A. niger* plate, into 50 ml of YEG (5 g/L yeast extract plus 20 g/L glucose) broth in a 250 ml, 4-baffle shake flask. The agar plug was incubated at 30°–37° C. for 16–20 hours at 200 rpm, mycelia was harvested through a sterile Miracloth filter and washed with Solution A. Washed mycelia was aseptically transferred into 40 ml of protoplasting solution and incubated at 30° C., 200 rpm, for 1–2 hours, protoplasting progress was monitored microscopically. The protoplasting reaction was filtered through sterile Miracloth, into two 50 ml sterile disposable centrifuge tubes and the volume brought up to 45 mls each with Solution B. The protoplasts were centrifuged at 2500 rpm for 5 minutes to obtain pellets and the supernatant was discarded. The pellet was washed twice more with 20 ml volumes of Solution B. The pellet was resuspended in 10 ml Solution B and protoplasts counted using a haemocytometer. Protoplasts were again centrifuged and the supernatant discarded. Protoplasts were resuspended, in Solution B to yield $\sim 1 \times 10^7$/100 µl. On ice, 100 µl protoplast solution was added to pre-chilled 15 ml tubes, one tube per transformation. 10 µg DNA was added in a volume not exceeding 10 µl. Solution C (12.5 µl) was added, mixed gently, and incubated on ice for 20 minutes.

MMS top agar (3 tubes of 10 ml each, per transformation) was melted and maintained at 55° C. Protoplasts were removed from the ice and Solution C (1 ml) and Solution B (2 ml) were added to each tube and the tubes were mixed gently. 1 ml of the protoplast mixture was added to each of the 3 top agar tubes and the top agar was poured onto MMS plates. This was repeated for each transformation and plates were incubated for 4–7 days at 30° C.

Solution A (per 500 ml)—0.44 g $K_2HPO_4$; 0.34 g $KH_2PO_4$; 48.156 g anhydrous $MgSO_4$ (FW 120.37); and $dlH_2O$ added for a final volume of 500 ml, pH 5.5. Filter sterilized and store at room temperature.

Protoplasting solution—Dissolved 180 units beta-D-glucanase (InterSpex Products, Inc) in 40 ml Solution A. Filter sterilized, 0.2 micron.

Solution B (per 500 ml)—5 ml 1M Tris, pH 7.5; 2.77 g $CaCl_2$ (FW 110.99); 109.32 g Sorbitol (FW 182.2; 1.2M); and $dlH_2O$ added for a final volume of 500 ml.

Filter sterilized and store at room temperature.

Solution C (per 500 ml)—250 g PEG 4000; 2.77 g $CaCl_2$; 5 ml 1 M Tris, pH 7.5; and $dlH_2O$ added for a final volume of 500 ml. Filter sterilized.

MMS Agar*—Dissolved in 1 L $dlH_2O$, 6 g/L $NaNO_3$; 0.52 g/L KCl; 1.52 g/L $KH_2PO_4$; 218.5 g/L D-Sorbitol; 1 ml/L Trace elements (see below); 10 g/L agar (low melt agarose in the top agar). Autoclave. Post-sterilization, aseptically added 10 ml 50% glucose and 1.25 ml 20% $MgSO_4.7H_2O$.

*For amdS selection, replace the nitrate in the MMS with 0.59 g/L acetamide and 3.4 g/L CsCl.

Trace Elements Solution
Dissolve in 250 ml $dlH_2O$,
1 g/L $FeSO_4.7H_2O$
8.8 g/L $ZnSO_4.7H_2O$
0.4 g/L $CuSO_4.5H_2O$
0.15 g/L $MnSO_4.4H_2O$
0.1 g/L $Na_2B_4O_7.10H_2O$
50 mg/L $(NH_4)_6Mo_7O_{24}.4H_2O$
Mix and added 0.2 ml concentrated HCl to dissolve. Brought volume up to 1 L with $dlH_2O$. Filter sterilized.

EXAMPLE 5

Figure 5:
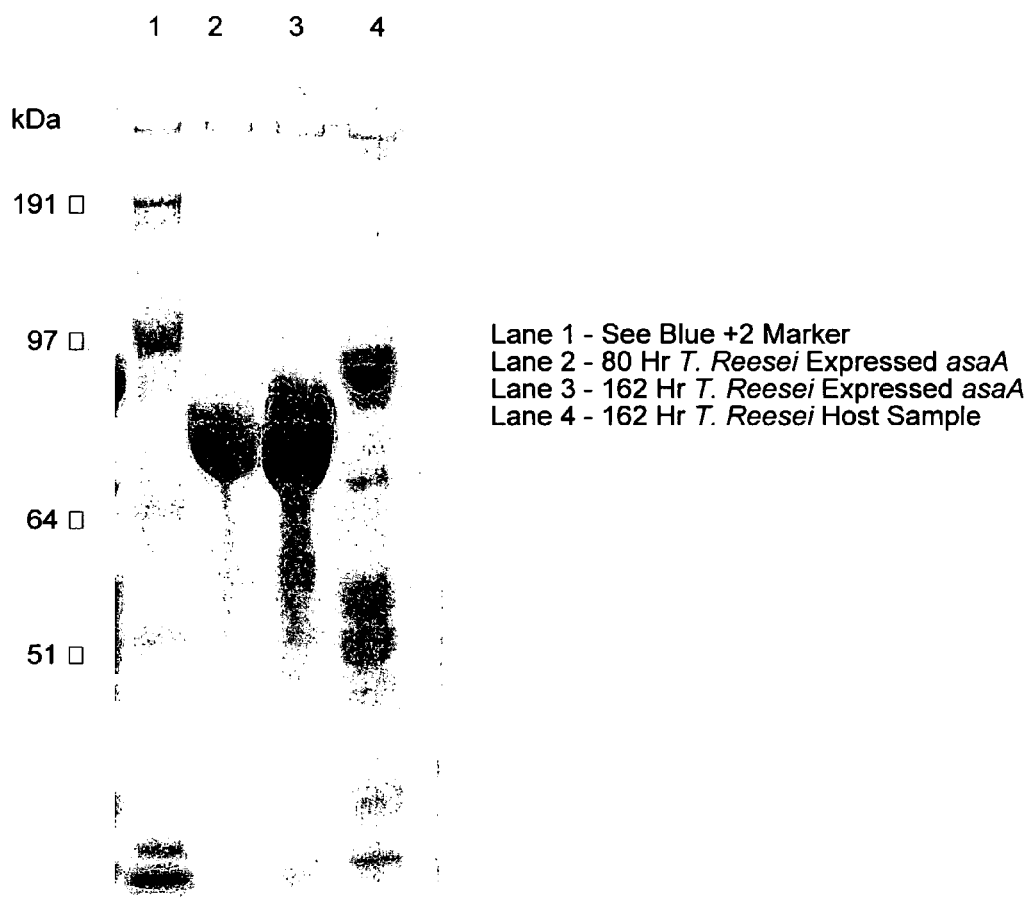
FIG. 5 provides an SDS-PAGE gel indicating the expression of asaA from *Trichoderma reesei* in a representative fermentation run for *Trichoderma reesei* clones as described in Example 5. Lane 1 represents the standard See Blue +2 marker; lane 2 represents *T. reesei* expressed AsaA after 80 hours; lane 3 represents *T. reesei* expressed AsaA after 162 hours and lane 4 represents a *T. reesei* host cell control at 162 hours in which the host cell has not been transformed with the asaA. An AsaA protein band is clearly observed at about 90 kDa and this band is absent in the host strain control.

Fermentation of *T. reesei* Transformed with the asaA Gene and Assay of Activity in *T. reesei* Clones In general, the fermentation protocol as described in Foreman et al. (Foreman et al. (2003) *J. Biol. Chem* 278:

31988–31997) was followed. More specifically, duplicate fermentations were run for each of the strains displayed in FIG. 5. 0.8 L of Vogels minimal medium (Davis et al., (1970) METHODS IN ENZYMOLOGY 17A, pg 79–143 and Davis, Rowland, NEUROSPORA, CONTRIBUTIONS OF A MODEL ORGANISM, Oxford University Press, (2000)) containing 5% glucose was inoculated with 1.5 ml frozen spore suspension. After 48 hours, each culture was transferred to 6.2 L of the same medium in a 14 L Biolafitte fermenter. The fermenter was run at 25° C., 750 RPM and 8 standard liters per minute airflow. One hour after the initial glucose was exhausted, a 25% (w/w) lactose feed was started and fed in a carbon limiting fashion to prevent lactose accumulation. The concentrations of glucose and lactose were monitored using a glucose oxidase assay kit or a glucose hexokinase assay kit with beta-galactosidase added to cleave lactose, respectively (Instrumentation Laboratory Co., Lexington, Mass.). Samples were obtained at regular intervals to monitor the progress of the fermentation. Collected samples were spun in a 50 ml centrifuge tube at ¾ speed in an International Equipment Company (Needham Heights, Mass.) clinical centrifuge. Sample supernatants were run of 4–12% BIS-TRIS SDS-PAGE gels, under reducing conditions with MOPS (morpholinepropanesulfonic acid) SDS running buffer and LDS sample buffer (FIG. 5).

EXAMPLE 6

Comparison of pH Stability of Native and Recombinant *A. kawachi* Acid-Stable Alpha Amylase Having GSH Activity (asaA)

Figure 6:
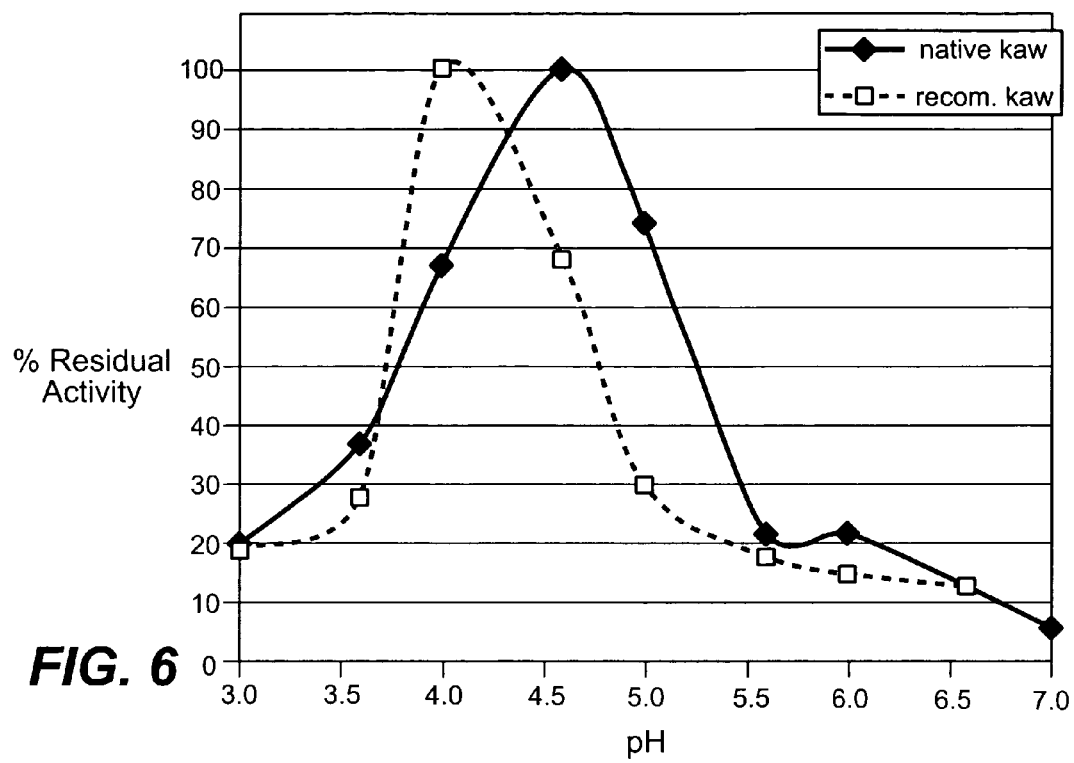
FIG. 6 illustrates the pH stability as % residual activity for the native *Aspergillus kawachi* (nAk-AsaA) and the expressed *A. kawachi* (rAk-AsaA) in the *T. reesei* host (SEQ ID NO:3), as described in Example 6.

Samples of recombinantly produced asaA (Tr-asaA) as described above and samples of native asaA were diluted to equal protein concentrations with 20 mM acetate buffer at pH 4.5. Reactions were run in 100 mM citrate/NaOH buffers at 50° C. for 30 minutes at pH levels 3 to 7. 1.0 mL of the reaction was added to 5 mL of 10% corn starch (Cargill Foods, Minn.) in 100 mM acetate, pH 4.5 in sample tubes. The tubes were shaken at 50° C. for 20 minutes. Then 0.5 mL 2.0% NaOH was added. Tubes were spun and 0.5 mL of the supernatant were assayed for reducing sugars using the Dinito Salicylic Acid (DNS) Assay (Goto et al., (1994) supra). The results are depicted in FIG. 6. The r-asaA exhibited 100% residual activity at pH 3.9. In comparison the n-asaA exhibited 100% residual activity at pH 4.5.

EXAMPLE 7

Effect of Tr-asaA Concentrations During Simultaneous Saccharification and Fermentation (SSF) of Non-Cooked Whole Ground Corn Substrate Tr-asaA was evaluated at two levels of glucoamylase (GA) from a cell free culture filtrate (0.5 and 1.0 GAU/g). Thirty six percent corn flour slurry was prepared containing dry corn steep (2.5% of corn flour). The pH of the slurry was adjusted to 4.8 with dilute sulfuric acid. The total dry solids of the slurry were 33.85%. Fermentations were carried out in 125 ml flasks containing 100 gm of mash (slurry). The desired levels of enzymes were added then 3 ml of propagated yeast slurry was added to start the fermentation. The yeast inoculum was prepared by adding 0.26 gm of dry Fali yeast to 100 gm of mash containing GA activity at 0.9 GAU/g of raw material solids. This slurry was placed in a 32° C. water bath and gently mixed for about 17 hours. At various time intervals samples of the fermentation (beer) were taken for HPLC analysis. After 72 hours the fermentations was terminated and the beer was dried at 60° C. to obtain the DDGS.

The starch content of the DDGS was determined and the insoluble solids of the beer after terminating the fermentation were spot checked for starch by the addition of Iodine. The enzymes used in this study were *A. niger* GA. Table 1 summarizes ethanol levels, iodine stain of the mash solids and % starch of the DDGS.

TABLE 1

Effect of asaA During Conversion of Granular Corn Starch to Ethanol under Yeast Fermentation Conditions

| GA GAU/g | asaA SSU/g | % v/v EtOH 24 hr | % v/v EtOH 50 hr | % v/v EtOH 72 hr | % starch DDGS | Iodine |
|---|---|---|---|---|---|---|
| 0.5 |      | 7.7  | 11.4 | 13.7 | 27.4 | + |
| 0.5 | 0.25 | 9.2  | 14.7 | 16.9 | 7.7  | + |
| 0.5 | 0.50 | 9.6  | 15.4 | 17.0 | 5.7  | +/− |
| 0.5 | 1.0  | 10.0 | 16.2 | 17.3 | 4.1  | +/−− |
| 0.5 | 2.0  | 10.9 | 16.5 | 17.5 | 2.8  | − |
| 0.5 | 3.0  | 11.2 | 16.8 | 17.5 | 1.6  | − |
| 0.5 | 4.0  | 11.2 | 16.9 | 17.4 | 1.7  | − |
| 0.5 | 5.0  | 11.2 | 17.0 | 17.7 | 1.5  | − |
| 1.0 |      | 9.3  | 14.4 | 16.2 | 13.0 | + |
| 1.0 | 0.25 | 11.6 | 17.1 | 17.8 | 3.6  | +/−− |
| 1.0 | 0.5  | 12.1 | 16.8 | 17.9 | 2.6  | − |
| 1.0 | 1.0  | 12.7 | 17.2 | 17.7 | 2.2  | − |
| 1.0 | 2.0  | 12.7 | 17.6 | 17.8 | 1.6  | − |
| 1.0 | 3.0  | 12.9 | 17.5 | 17.8 | 1.1  | − |
| 1.0 | 4.0  | 13.2 | 17.5 | 17.9 | 0.8  | − |
| 1.0 | 5.0  | 13.3 | 17.2 | 17.9 | 1.1  | − |
| 2.0 |      | 11.2 | 15.5 | 16.9 | 9.6  | + |
| 3.0 |      | 11.4 | 15.9 | 17.2 | 5.8  | + |

The results as illustrated in Table 1 demonstrate Tr-asaA enhanced the hydrolysis of granular corn starch by glucoamylase.

EXAMPLE 8

Conversion of Granular Starch Substrates by Glucoamylase and Alpha Amylases

Commercial alpha amylases from different sources were compared with Tr-asaA under the simultaneous saccharification and fermentation conditions in the presence of glucoamylase at 0.5 GAU/g of ds. The activity of the commercial alpha amylases was determined using the soluble starch substrate (SSU) method assay as described earlier.

TABLE 2

| Alpha Amylase | Microbial Strain | SSU/ml |
|---|---|---|
| Tr-asaA | *A. kawachi* asAA expressed in *T. reesei* | 90 |
| SPEZYME LT AA | *Bacillus amyloliquefaciens* | 2,759 |
| SPEZYME FRED | *Bacillus licheniformis*** | 4,842 |
| SPEZYME Ethyl | *Bacillus stereothermophilus*** | 22,082 |
| CLARASE L | *Aspergillus oryzae* | 23,087 |

**denotes a recombinant strain

Figure 7:
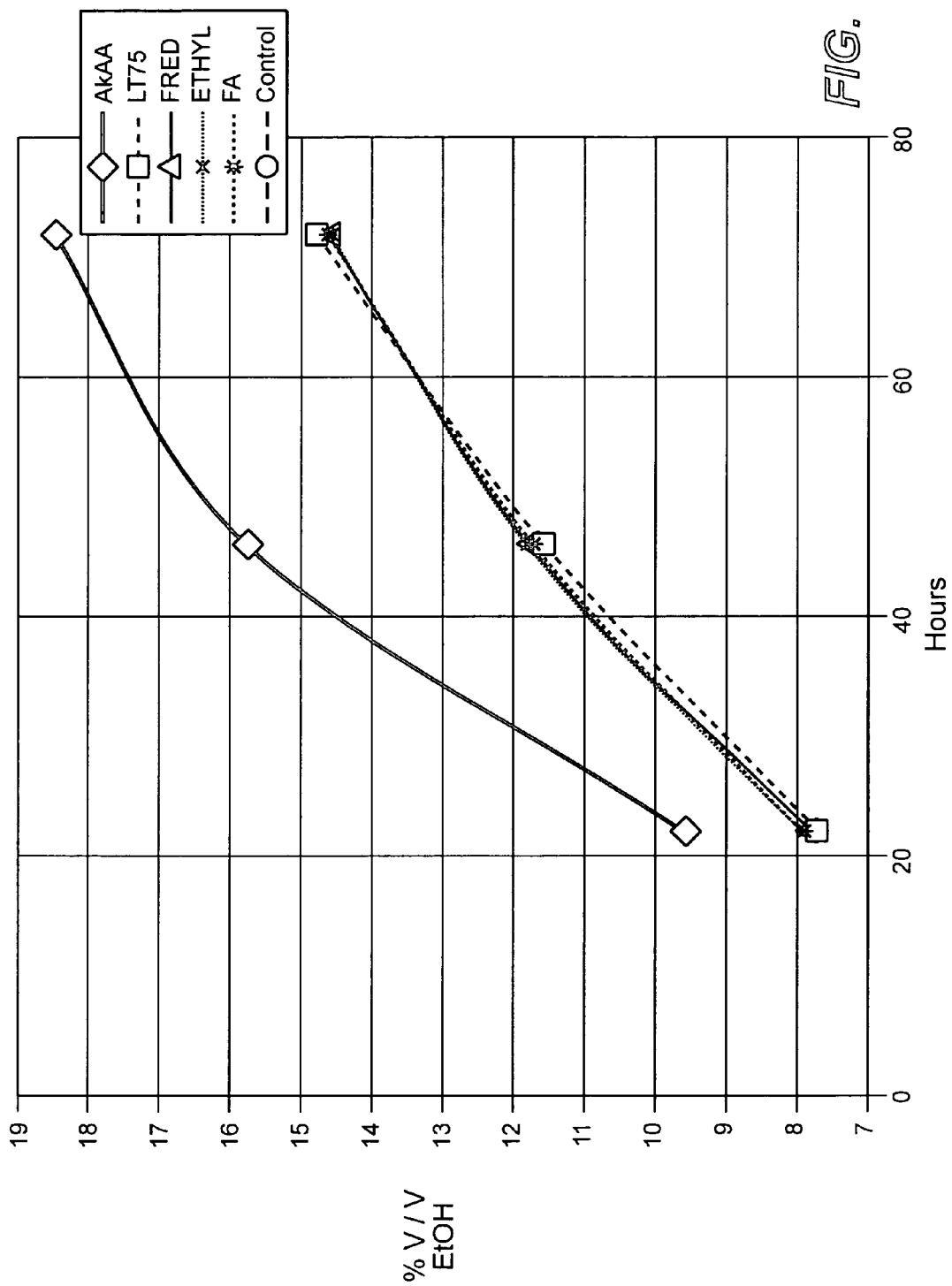
FIG. 7 illustrates the % (v/v) ethanol (EtOH) production from the fermentation of corn flour mash at pH 5.0 with glucoamylase (0.5 GAU/h DISTILLASE) and an alpha amylase over time, wherein Tr-AsaA (*A. kawachi* acid stable alpha amylase expressed in *Trichoderma reesei*) is represented by AKAA; SPEZYME LT75 alpha amylase is represented by LT75; SPEZYME FRED is represented by FRED; SPEZYME ETHYL is represented by ETHYL; CLARLASE is represented by FA and DISTILLASE is the control. Reference is made to Example 8.

Ethanol fermentation was carried out using whole ground corn as described in Example 7. Alpha amylases from the sources listed in Table 2 were added at 1.0 SSU/gram of ground corn and glucoamylase at 0.5 GAU/g. The samples were taken during the course of the fermentation and analyzed for ethanol content (FIG. 7). After the fermentation, the insoluble solids (DDGS) were separated and the residual starch content of the corn mash at pH 5.0 was determined. The results are summarized in Table 3.

TABLE 3

| | | Ave % v/v EtOH | | | |
|---|---|---|---|---|---|
| GAU/g | Alpha Amylase at (1.0 SSU/g) | 22 hr | 46 hr | 72 hr | Residual % starch in DDGS 72 hr |
| 0.5 | — | 7.77 | 11.56 | 14.44 | 29.8 |
| 0.5 | SPEZYME LT-AA | 7.72 | 11.56 | 14.78 | 30.8 |
| 0.5 | SPEZYME FRED | 7.84 | 11.77 | 14.59 | 30.8 |
| 0.5 | SPEZYME Ethyl | 7.94 | 11.82 | 14.57 | 29.1 |
| 0.5 | CLARASE L | 7.94 | 11.72 | 14.62 | 30.8 |
| 0.5 | Tr-asaA | 9.57 | 15.75 | 18.44 | 9.0 |

The results in Table 3 clearly show that Tr-asaA is very effective in aiding glucoamylase to hydrolyze granular starch under the ethanol fermentation conditions using yeast. Additionally, as observed from the table, % ethanol produced in the fermentation (18.44) is greater and % residual starch in DDGS (9.0) is significantly lower using the enzyme combination of the present invention.

EXAMPLE 9

Evaluation of Whole Ground Wheat in the Ethanol Fermentation Using Tr-AsaA

To a 36% slurry of whole ground wheat, dry corn steep liquor was added at 2.5% based on the weight of the whole ground wheat. The fermentations were carried out in 125 ml flasks containing 100 gm of mash. The pH of the slurry was adjusted to 4.8 with dilute sulfuric acid. The mash was diluted to a final concentration of 33.85% ds.

Glucoamylase (0.5 GAU/g ground wheat) and asaA (1.0 SSU/g whole ground wheat) were added to the mash. This was followed by adding 3.0 ml of propagated yeast to start the fermentation. Yeast inoculum was prepared by adding 0.26 gm of dry Fali yeast to 100 gm of mash. The fermentations were run in a 32° C. water bath while gently stirred. At various time intervals samples of the fermentation broth (beer) were taken, centrifuged for HPLC analysis of sugar composition and ethanol (Table 4)

TABLE 4

Whole ground wheat granular starch in the yeast fermentation for ethanol production

| GA GAU/g | Tr-asaA SSU/g | Hrs | % w/v DP > 2 | % w/v DP-2 | % w/v DP-1 | % w/v Lactic | % w/v Glycerol | % v/v Ethanol |
|---|---|---|---|---|---|---|---|---|
| | | 0 | 0.98 | 0.97 | 2.00 | 0.22 | 0.12 | 0.00 |
| 0 | 0 | 24 | 1.33 | 0.00 | 0.02 | 1.09 | 0.15 | 2.42 |
| 0 | 0 | 48 | 1.17 | 0.00 | 0.00 | 1.39 | 0.13 | 2.38 |
| 0 | 0 | 72 | 1.08 | 0.00 | 0.01 | 1.38 | 0.13 | 2.16 |
| 0 | 0.1 | 24 | 1.30 | 0.00 | 0.02 | 1.06 | 0.16 | 4.49 |
| 0 | 0.1 | 48 | 1.16 | 0.00 | 0.02 | 1.51 | 0.16 | 2.28 |
| 0 | 0.1 | 72 | 1.23 | 0.00 | 0.01 | 1.83 | 0.15 | 2.91 |
| 0 | 0.25 | 24 | 1.28 | 0.03 | 0.02 | 1.06 | 0.17 | 2.94 |
| 0 | 0.25 | 48 | 1.05 | 0.00 | 0.02 | 1.41 | 0.15 | 2.73 |
| 0 | 0.25 | 72 | 1.24 | 0.00 | 0.03 | 1.92 | 0.17 | 3.06 |
| 0 | 0.5 | 24 | 1.25 | 0.00 | 0.01 | 1.02 | 0.13 | 3.03 |
| 0 | 0.5 | 48 | 1.22 | 0.00 | 0.02 | 1.60 | 0.18 | 3.27 |
| 0 | 0.5 | 72 | 1.26 | 0.00 | 0.03 | 1.90 | 0.18 | 3.24 |
| 0 | 0.75 | 24 | 1.29 | 0.03 | 0.02 | 1.06 | 0.16 | 3.21 |
| 0 | 0.75 | 48 | 1.29 | 0.00 | 0.03 | 1.62 | 0.10 | 3.57 |
| 0 | 0.75 | 72 | 1.34 | 0.00 | 0.03 | 1.90 | 0.18 | 3.60 |
| 0 | 1.0 | 24 | 1.29 | 0.04 | 0.02 | 1.04 | 0.16 | 3.43 |
| 0 | 1.0 | 48 | 1.32 | 0.04 | 0.01 | 1.55 | 0.18 | 4.02 |
| 0 | 1.0 | 72 | 1.46 | 0.09 | 0.04 | 1.84 | 1.21 | 4.15 |
| 0.2 | 0 | 24 | 1.18 | 0.00 | 0.00 | 1.04 | 0.18 | 3.34 |
| 0.2 | 0 | 48 | 1.16 | 0.00 | 0.02 | 1.67 | 0.19 | 4.14 |
| 0.2 | 0 | 72 | 1.16 | 0.00 | 0.02 | 1.92 | 0.19 | 4.78 |
| 0.2 | 0.1 | 24 | 1.20 | 0.00 | 0.03 | 1.05 | 0.20 | 3.64 |
| 0.2 | 0.1 | 48 | 1.12 | 0.00 | 0.02 | 1.59 | 0.20 | 4.60 |
| 0.2 | 0.1 | 72 | 1.14 | 0.00 | 0.03 | 1.86 | 0.21 | 5.58 |
| 0.2 | 0.25 | 24 | 1.16 | 0.00 | 0.03 | 1.02 | 0.21 | 3.80 |
| 0.2 | 0.25 | 48 | 1.14 | 0.00 | 0.03 | 1.57 | 0.22 | 5.13 |
| 0.2 | 0.25 | 72 | 1.06 | 0.03 | 0.03 | 1.71 | 0.21 | 5.90 |
| 0.2 | 0.5 | 24 | 1.20 | 0.00 | 0.03 | 1.03 | 0.22 | 4.04 |
| 0.2 | 0.5 | 48 | 1.14 | 0.00 | 0.01 | 1.54 | 0.22 | 5.61 |
| 0.2 | 0.5 | 72 | 1.13 | 0.03 | 0.04 | 1.74 | 0.23 | 6.65 |
| 0.2 | 0.75 | 24 | 1.16 | 0.00 | 0.03 | 1.03 | 0.22 | 4.13 |
| 0.2 | 0.75 | 48 | 1.24 | 0.00 | 0.04 | 1.54 | 0.24 | 5.68 |
| 0.2 | 0.75 | 72 | 1.10 | 0.00 | 0.01 | 1.63 | 0.23 | 7.14 |
| 0.2 | 1.0 | 24 | 1.00 | 0.00 | 0.03 | 0.96 | 0.17 | 4.14 |

TABLE 4-continued

Whole ground wheat granular starch in the yeast fermentation for ethanol production

| GA GAU/g | Tr-asaA SSU/g | Hrs | % w/v DP > 2 | % w/v DP-2 | % w/v DP-1 | % w/v Lactic | % w/v Glycerol | % v/v Ethanol |
|---|---|---|---|---|---|---|---|---|
| 0.2 | 1.0 | 48 | 1.16 | 0.00 | 0.04 | 1.50 | 0.25 | 5.90 |
| 0.2 | 1.0 | 72 | 1.21 | 0.03 | 0.04 | 1.68 | 0.23 | 6.76 |
| 0.5 | 0 | 24 | 1.07 | 0.00 | 0.03 | 0.98 | 0.24 | 4.50 |
| 0.5 | 0 | 48 | 1.01 | 0.00 | 0.02 | 1.41 | 0.25 | 6.29 |
| 0.5 | 0 | 72 | 1.10 | 0.03 | 0.15 | 1.55 | 0.25 | 7.49 |
| 0.5 | 0.1 | 24 | 1.12 | 0.00 | 0.04 | 0.94 | 0.24 | 4.62 |
| 0.5 | 0.1 | 48 | 1.12 | 0.00 | 0.03 | 1.34 | 0.27 | 6.92 |
| 0.5 | 0.1 | 72 | 1.09 | 0.03 | 0.03 | 1.46 | 0.27 | 8.45 |
| 0.5 | 0.25 | 24 | 1.17 | 0.00 | 0.05 | 0.97 | 0.27 | 5.01 |
| 0.5 | 0.25 | 48 | 1.20 | 0.00 | 0.04 | 1.28 | 0.28 | 7.18 |
| 0.5 | 0.25 | 72 | 1.06 | 0.03 | 0.03 | 1.34 | 0.27 | 8.78 |
| 0.5 | 0.5 | 24 | 1.16 | 0.00 | 0.05 | 0.91 | 0.26 | 5.29 |
| 0.5 | 0.5 | 48 | 1.11 | 0.00 | 0.04 | 1.18 | 0.28 | 7.71 |
| 0.5 | 0.5 | 72 | 1.07 | 0.03 | 0.04 | 1.23 | 0.28 | 9.47 |
| 0.5 | 0.75 | 24 | 1.15 | 0.00 | 0.05 | 0.90 | 0.28 | 5.33 |
| 0.5 | 0.75 | 48 | 1.11 | 0.03 | 0.06 | 1.16 | 0.30 | 8.08 |
| 0.5 | 0.75 | 72 | 1.06 | 0.04 | 0.05 | 1.17 | 0.30 | 9.91 |
| 0.5 | 1.0 | 24 | 1.12 | 0.00 | 0.06 | 0.89 | 0.29 | 5.52 |
| 0.5 | 1.0 | 48 | 1.12 | 0.00 | 0.05 | 1.14 | 0.32 | 8.39 |

EXAMPLE 10

Effect of Substrate Treatment on the Ethanol Yield and Composition of Distilleries Dry Grain Solids, (DDGS)

Whole ground corn substrate was subjected to a conventional dry milling process for fuel alcohol fermentation using a hammer mill to reduce particle size. Three different mashes were prepared.

Treatment 1 (Trt 1) is a high temperature treatment, which involved a batch liquefaction of a 36% ds corn flour slurry containing 0.9% dry corn steep (DCS) with 3.5 U/g SPEZYME ETHYL at pH 5.6 by jet cooking according to the prior art procedures. The slurry was place in a 90° C. bath for 1.5 hours, mixed and then cooled to 30° C. with a pH adjustment to 5.0 with dilute sulfuric acid. The slurry was further diluted with water to 32.71% ds.

Treatment 2 (Trt 2) is a low temperature treatment. The mash was prepared by incubating a 36% corn flour slurry containing 0.9% DCS with the pH adjusted to 5.0 with dilute sulfuric acid at 60° C. for three hours. Prior to incubation 0.05 GAU/g of glucoamylase was added.

Treatment 3 (Trt 3) is a room temperature treatment—a corn slurry was obtained at room temperature prior to use in the fermentation with 0.5 GAU glucoamylase/g of corn and 1.0 SSU/g corn of Tr-asaA.

Yeast fermentation was then carried out on each treatment as described in example 7.

After the fermentation, ethanol yield was determined and the insoluble solids from each treatment were separated by centrifugation, dried at 60° C. and the total carbohydrate content and nitrogen content were determined. The results are illustrated in Table 5, wherein Trt 3 is a process encompassed by the invention.

TABLE 5

Comparison of ethanol yield and the composition of DDGS of different treatments of whole ground corn substrate under ethanol fermentation using yeast

| Corn Mash Treatment | Kgs DDGS/MT corn | % Residual starch content in DDGS | % Total Protein in DDGS | Ethanol L/MT corn |
|---|---|---|---|---|
| Trt 1 High Temperature | 326 | 4.8 | 27.5 | 402 |
| Trt 2 Low Temperature | 299 | 3.8 | 29.5 | 429 |
| Trt 3 No heat treatment GA + Tr-asaA | 274 | 3.5 | 31.6 | 438 |

As observed from the results illustrated in Table 5, the % residual starch in DDGS treated according to the process of the present invention (Trt 3) was less than the % residual starch obtained from the prior art treatment (Trt 1) or the low temperature treatment (Trt 2). The values were 3.5% (Trt 3) as opposed to 4.8% or 3.8% for Trt1 and Trt 2. The total protein content of the DDGS and the amount of ethanol produced was higher from Trt 3 according to the invention as compared to the prior art treatment (Trt 1).

EXAMPLE 11

Incubation of Granular Corn Starch with Purified *Aspergillus kawachi* Alpha Amylase and Purified *Aspergillus Niger* Glucoamylase.

Enzyme Purification:

*Aspergillus niger* glucoamylase (GA) and *Aspergillus kawachi* alpha amylase (AkAA) were both purified from culture filtrate using a preparative high pressure liquid chromatographic (HPLC) method using an AKTA (Amersham Pharmacia, Biotech., NJ). In a typical experiment, both crude enzyme samples were desalted with 10 mM MES buffer (pH 5.75) to bring down the conductivity using a spin column (Bio-Rad, Calif.). The samples were brought up to 2M $NH_4SO_2$. The sample was loaded on to a Q-Sepharose column (Amersham, Biosciences, NJ) and eluted with 20 mM MES buffer (pH 5.75) using a gradient of 1.5 M KCl. The fractions with corresponding activity were pooled together and concentrated for further experiments.

Incubation with Granular Corn Starch with Purified Enzymes:

The purified enzyme preparations were added to a 4.0% granular corn starch (Cargill, Minneapolis, Minn.) in 0.1 M acetate buffer (pH 4.5) as follows for Scanning Electron Microscopic (SEM) analysis.

Purified GA at 0.5 GAU/g corn starch; purified AkAA at 1.0 SSU/g starch; and GA and AkAA combined were incubated at 32° C. with gentle stirring. Aliquot samples (0.75 ml) were taken at intervals of 2, 4 and 8 hours, centrifuged and the soluble sugar determined by the method described in the examples above. The pellet was resuspended in distilled water (5 ml) and centrifuged. The pellet was suspended again in 5 ml of absolute ethanol (99%), stirred for uniform mixing and centrifuged. The alcohol treated pellet was air-dried in the tube and used for SEM analysis.

SEM Analysis:

Approximately 200 µl dry volume was transferred to a 1.5 ml Ependorf tube and 0.8 ml absolute ethanol was added. The components were vortexed to make a suspension of starch particles. A few drops of suspension was placed on a freshly cleaned glass cover slip and allowed to air dry. The cover slip was mounted on specimen stubs with carbon adhesive tabs, painted around the circumference with colloidal silver adhesive (Electron Microscopy Sciences, Ft. Washington, Pa.) and coated with a thin layer of gold in a ScanCoat Six Sputter Coater (Edwards High Vacuum Intl. Crawley, UK). Scanning electron microscopy was done at 5 kv in the secondary electron imaging mode using a Quanta 200 FEG scanning electron microscope (FEI Inc., Hillsboro, Ore) at instrumental magnification of 1,000 and 5,000×. Eight to ten images were made from different areas on each sample stub. The effect of individual and combined enzyme treatments on the granular corn starch is illustrated in FIGS. 8 and 9.

Figure 8:
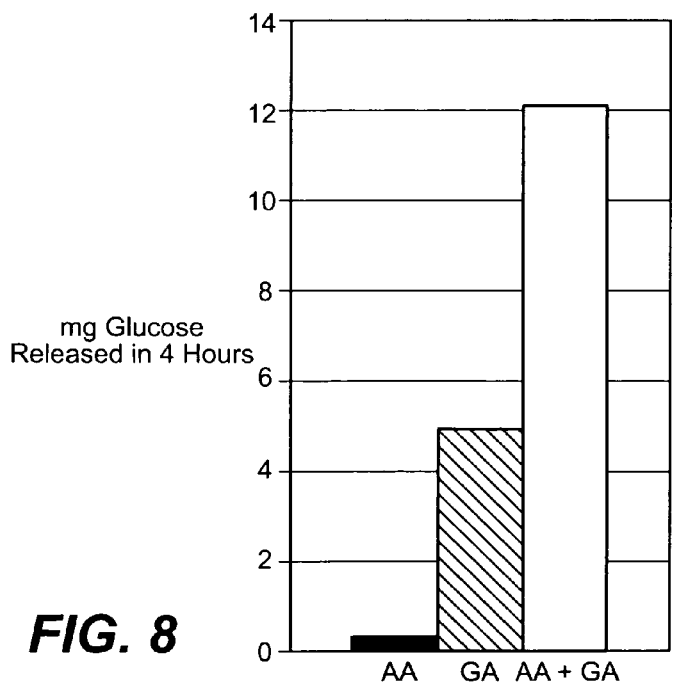
FIG. 8 illustrates the degradation of granular starch as glucose released after 4 hours with incubated purified DISTILLASE (GA), purified AkAA (*A. kawachi* acid stable alpha amylase expressed in *Trichoderma reesei*), and the combination of AkAA and GA at pH 5.0. Reference is made to Example 11.
Figure 9:
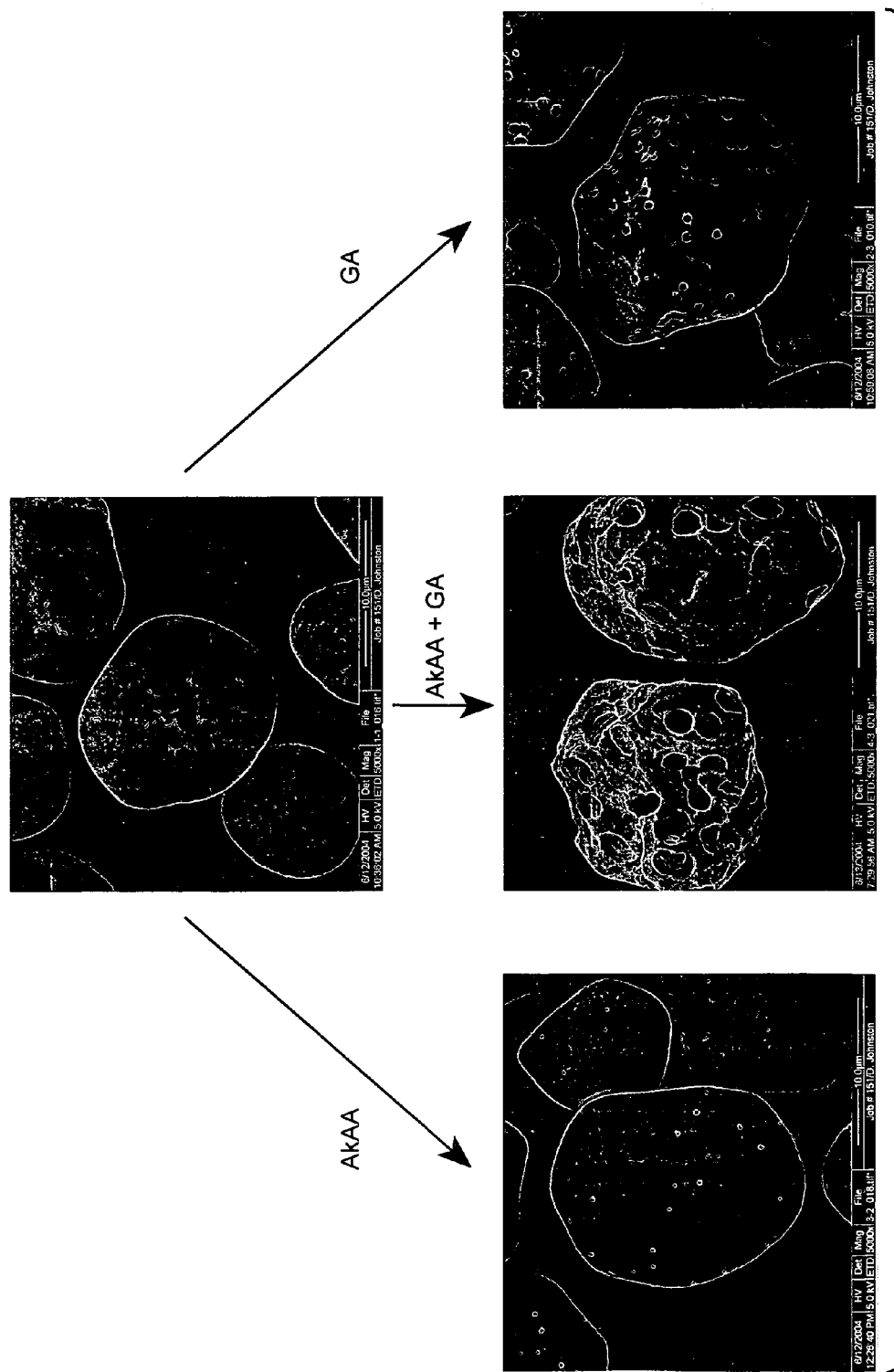
FIG. 9 illustrates SEMs of granular corn starch incubated with the enzymes described for FIG. 8: purified DISTILLASE (GA), purified AkAA (*A. kawachi* acid stable alpha amylase expressed in *Trichoderma reesei*), and the combination of AkAA and GA.

Hydrolysis and Microscopic Examination:

Reducing sugar (mg/ml reducing equivalents), measured as glucose released after 4 hours as a result of granular starch hydrolysis by AkAA and GA is illustrated in FIG. 8. Degradation of granular starch with glucoamylase alone was 4.9 mg/ml; degradation of granular starch with AkAA alone was only 0.3 mg/ml. However, degradation of granular starch with the combination of GA and AkAA was 12.1 mg/ml. The degradation value for the enzymes combined illustrates a synergistic interaction, which is significantly greater than the additive value of the enzymes.

The starch granules treated as described in this example were observed with a scanning electron microscope. As shown in FIG. 9, corn starch granules incubated with purified AkAA did show minor surface modification. These were observed as small pin prick holes. Corn starch granules incubated with purified GA showed many small defined deep holes. Significantly, corn starch granules incubated with the combination of GA and AkAA showed numerous wide and deep penetrating cavities. Additionally, surface erosion, which exposed the layered structure of the granular center, was observed in the granules incubated with the combination of GA and AkAA.

EXAMPLE 12

Effect of % Dry Solids Content (ds) of a Granular Corn Starch Slurry on Ethanol Yield Corn flour was slurried with water to obtain a 36% ds mash. A small amount of corn steep (0.2% of the slurry) was added along with 400 ppm (0.04%) urea to the mash prior to adjusting the pH to 4.5 with sulfuric acid. The dry solids content of the slurry was adjusted from 20 to 36% ds. The fermentations were carried out in 125 ml flasks containing a total of 100 g mash. The enzymes were diluted so that a constant volume of 0.5 ml was used for each enzyme. Each flask was inoculated with 3 ml of yeast that was propagated 17 hours prior to use. The yeast propagation procedure involved adding 0.5% dry Fali yeast to 25% ds mash containing 0.5 GAU/g of GA and 1.5 SSU/g AkAA and incubating while gently mixing in a 32° C. water bath. At approximately 24 hour time intervals samples of beer were dried at 60° C. to obtain DDGS.

TABLE 6

Effect of DS Content on the Ethanol Production and Residual Starch in DDGS at 75 hours

| | GA (0.5 GAU/g) | | AkAA (1.5 SSU/g) + GA (0.5 GAU/g) | |
|---|---|---|---|---|
| % DS | % v/v EtOH | DDGS % residual starch | % v/v EtOH | DDGS % residual starch |
| 20 | 9.86 | 2.28 | 10.15 | 1.37 |
| 24 | 11.75 | 5.79 | 12.51 | 1.00 |
| 28 | 13.51 | 13.07 | 14.80 | 1.83 |
| 32 | 15.38 | 18.06 | 17.47 | 3.78 |
| 36 | 16.39 | 29.37 | 18.07 | 13.36 |

Figure 10A:
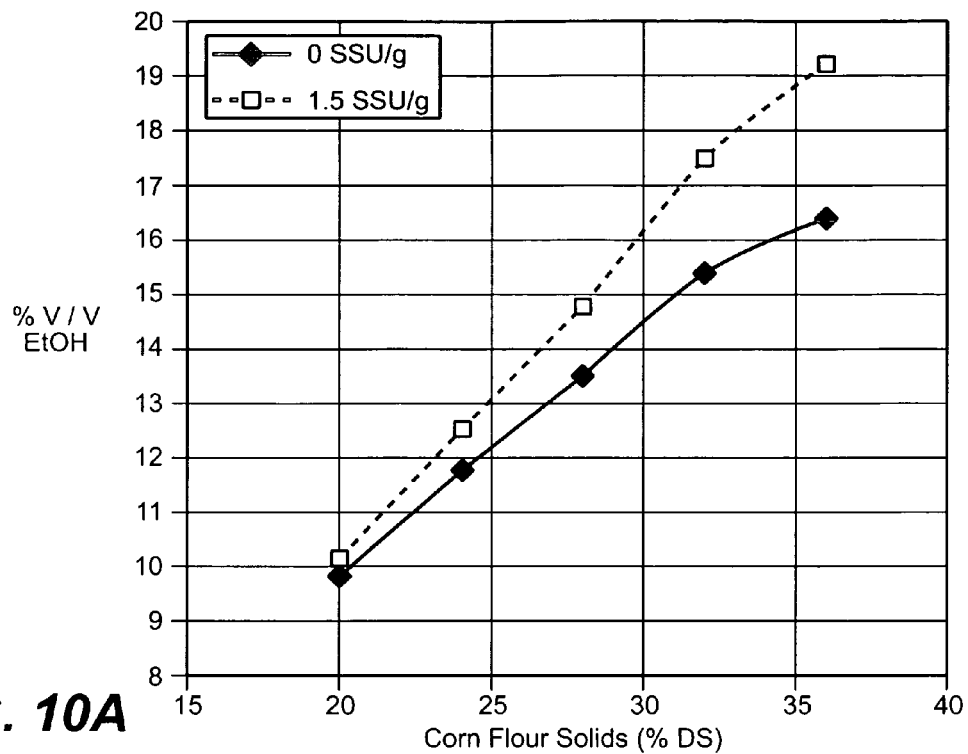
FIG. 10A summarizes the final ethanol level as % (v/v) at different corn flour solids (% ds) as measured at 72 hours in fermentation.
Figure 10B:
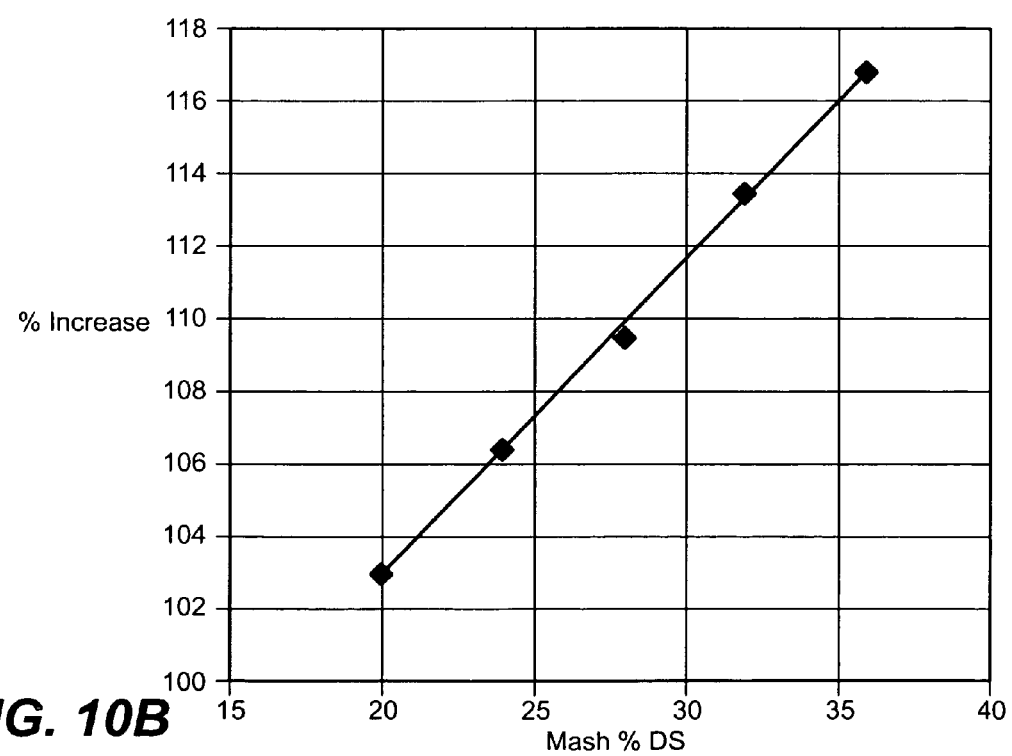
FIG. 10B illustrates the % increase in ethanol with AkAA for each corn mash solids (% ds) plotted against mash solids (% ds).

Almost all of the glucose (DP-1) generated during the fermentation was converted to ethanol except at the high solids (data not shown). For each % DS tested, the AkAA increased the rate and amount of ethanol. FIG. 10A summarizes the final ethanol level at each solids level and FIG. 10B shows the % increase in ethanol with AkAA for each solid against mash solids. Both figures demonstrate the positive effect AkAA has on hydrolyzing granular starch and particularly at high solids %. Also as observed in FIG. 10A, as the dissolved solids increase, the difference in the residual starch with and without AkAA also increases. As observed in FIG. 10B as the % ds in the corn slurry increases, the influence of AkAA on ethanol production increases.

Figure 11:
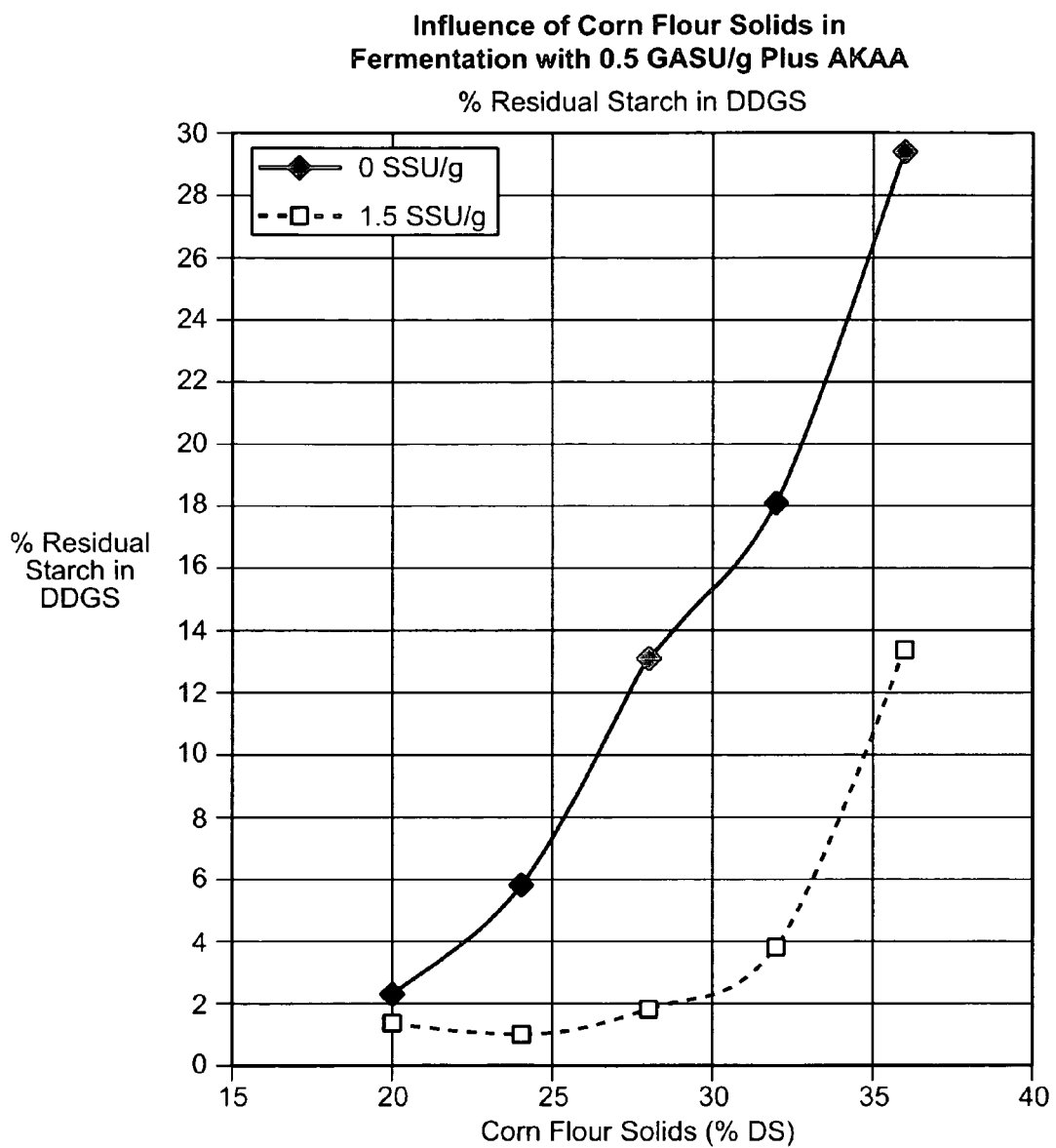
FIG. 11 illustrates the % residual starch produced from different corn flour solids in fermentation with 0.5 GAU/g and AkAA (0.0 SSU/hg or 1.5 SSU/hg) after 72 hours as further explained in example 12.

The results from Table 6 and FIG. 11 clearly show a benefit of using a composition of AkAA and GA in the methods of the invention. In all instances the % starch in the DDGS is decreased when the AkAA is used in combination with the GA and further the % starch found in DDGS from a corn starch substrate having a % ds as high as 36% is reduced by half when compared to the % starch in a DDGS without the addition of AkAA.

The invention claimed is:

1. A granular starch hydrolyzing enzyme composition comprising a) an isolated acid stable alpha amylase (asAA) having granular starch hydrolyzing activity and having the sequence of SEQ ID NO: 3 and b) a glucoamylase.

2. The enzyme composition of claim 1, wherein the asAA is produced in a *Trichoderma* host.

3. The enzyme composition of claim 2, wherein the *Trichoderma* host is *T reesei*.

4. The enzyme composition of claim 1, wherein said glucoamylase is derived from a filamentous fungal strain.

5. The enzyme composition of claim 4, wherein the filamentous fungal strain is derived from *Aspergillus, Trichoderma, Humicola* or *Rhizopus*.

6. The enzyme composition of claim 5, wherein the filamentous fungal strain is an *Aspergillus* strain.

7. The enzyme composition of claim 6, wherein the *Aspergillus* strain is *Aspergillus niger*.

8. The enzyme composition of claim 1, wherein the ratio of asAA to glucoamylase activity is 10:1 to 1:10.

9. The enzyme composition of claim 1, wherein the ratio of asAA to glucoamylase activity is 5:1 to 1:5.

10. The enzyme composition of claim 1 further comprising a third enzyme.

11. The enzyme composition of claim 10, wherein the third enzyme is selected from the group of proteases, pullulanases, cellulases and combinations thereof.

12. The enzyme composition of claim 1, wherein the enzyme composition is contemporaneously combined with a slurry of a granular starch substrate and ethanologenic microorganisms in a fermentation under suitable fermentation conditions to produce an alcohol.

13. The enzyme composition of claim 12, wherein the granular starch substrate is obtained from corn, wheat, sorghum, rye or rice.

14. The enzyme composition of claim 13, wherein the granular starch substrate is obtained from corn.

* * * * *